(12) United States Patent
Fadool

(10) Patent No.: US 11,746,391 B2
(45) Date of Patent: Sep. 5, 2023

(54) MUTATIONS IN RHODOPSIN GENE IN ZEBRAFISH AND USES THEREOF

(71) Applicant: The Florida State University Research Foundation Inc., Tallahassee, FL (US)

(72) Inventor: James Fadool, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 519 days.

(21) Appl. No.: 17/064,920

(22) Filed: Oct. 7, 2020

(65) Prior Publication Data

US 2021/0032709 A1     Feb. 4, 2021

Related U.S. Application Data

(62) Division of application No. 15/972,761, filed on May 7, 2018, now Pat. No. 10,907,220.

(60) Provisional application No. 62/501,934, filed on May 5, 2017.

(51) Int. Cl.

| | |
|---|---|
| *C12Q 1/6897* | (2018.01) |
| *A01K 67/027* | (2006.01) |
| *C12Q 1/6883* | (2018.01) |
| *C12N 15/85* | (2006.01) |
| *G01N 33/50* | (2006.01) |
| *G01N 33/68* | (2006.01) |
| *C07K 14/46* | (2006.01) |
| *C12N 15/10* | (2006.01) |
| *C07K 14/705* | (2006.01) |

(52) U.S. Cl.
CPC ........ *C12Q 1/6897* (2013.01); *A01K 67/0276* (2013.01); *C07K 14/461* (2013.01); *C07K 14/705* (2013.01); *C12N 15/102* (2013.01); *C12N 15/85* (2013.01); *C12Q 1/6883* (2013.01); *G01N 33/50* (2013.01); *G01N 33/6893* (2013.01); *A01K 2217/056* (2013.01); *A01K 2217/075* (2013.01); *A01K 2217/206* (2013.01); *A01K 2227/40* (2013.01); *A01K 2267/0306* (2013.01); *A01K 2267/0393* (2013.01); *C12N 2015/859* (2013.01); *G01N 2800/164* (2013.01)

(58) Field of Classification Search
CPC .............. C12Q 1/6897; A01K 67/0276; A01K 2217/075; A01K 2217/206; A01K 2227/40; A01K 2267/0306; A01K 2267/0393; C07K 14/461; C12N 2015/859

See application file for complete search history.

(56) References Cited

PUBLICATIONS

Adekeye, et al., Ablation of the proapoptotic genes chop or Ask1 does not prevent or delay loss of visual function in a P23H transgenic mouse model of retinitis pigmentosa. PLoS One 2, 2014, e83871.
Aguirre GD. Animal models as tools for screening candidate drugs. Retina 2005; 25: S36-7.
Aguirre GD. Concepts and strategies in retinal gene therapy. Invest. Ophthalmol. Vis. Sci. 2017; 58:5399-411.
Akimoto, et al., Targeting of GFP to newborn rods by nrl promoter and temporal expression profiling of flow-sorted photoreceptors. Proc.Natl.Acad.Sci.U.S.A. 2006; 103:3890-5.
Alvarez-Delfin, et al., Tbx2b is required for ultraviolet photoreceptor cell specification during zebrafish retinal development. Proc. Natl. Acad. Sci. U. S. A. 6, 2009, 2023-2028.
Aquirre G, et al., Rod-cone dysplasia in Irish setters: A defect in cyclic GMP metabolism in visual cells. Science 1978; 201:1133-4.
Armstrong, et al., Homology directed knockin of point mutations in the zebrafish tardbp and fus genes in ALS using the CRISPR/Cas9 system. PLoS One 2016; 11:e0150188.
Auer TO, et al., Highly efficient CRISPR/Cas9-mediated knock-in in zebrafish by homology-independent DNA repair. Genome Res. 2014; 24:142-53.
Bedell, V.M., Wang, Y., Campbell, J.M., Poshusta, T.L., Starker, C.G., Krug, R.G.,2nd, Tan, W., Penheiter, S.G., Ma, A.C., Leung, A.Y. et al. (2012). In vivo genome editing using a high-efficiency TALEN system. Nature 7422, 114-118.
Berson, E.L., Rosner, B., Weigel-DiFranco, C., Dryja, T.P., and Sandberg, M.A. (2002). Disease progression in patients with dominant retinitis pigmentosa and rhodopsin mutations. Invest. Ophthalmol. Vis. Sci. 9, 3027-3036.
Bourne MC, Campbell DA, Tansley K. Hereditary degeneration of the rat retina. Br.J.Ophthalmol. 1938; 22:613-23.
Branchek T, Bremiller R. The development of photoreceptors in the zebrafish, brachydanio rerio. I. structure. J.Comp.Neurol. 1984; 224:107-15.
Branchek T. The development of photoreceptors in the zebrafish, brachydanio rerio. II. function. J.Comp.Neurol. 1984; 224:116-22.
Brockerhoff SE, Hurley JB, Janssen-Bienhold U, Neuhauss SC, Driever W, Dowling JE. A behavioral screen for isolating zebrafish mutants with visual system defects. Proc.Natl.Acad.Sci.U.S.A. 1995; 92:10545-9.
Cade, L., Reyon, D., Hwang, W.Y., Tsai, S.Q., Patel, S., Khayter, C., Joung, J.K., Sander, J.D., Peterson, R.T., and Yeh, J.R. (2012). Highly efficient generation of heritable zebrafish gene mutations using homo- and heterodimeric TALENs. Nucleic Acids Res. 16, 8001-8010.
Chang B, Hawes NL, Pardue MT, German AM, Hurd RE, Davisson MT, Nusinowitz S, Rengarajan K, Boyd AP, Sidney SS, Phillips MJ, Stewart RE, Chaudhury R, Nickerson JM, Heckenlively JR, Boatright JH. Two mouse retinal degenerations caused by missense mutations in the beta-subunit of rod cGMP phosphodiesterase gene. Vision Res. 2007; 47:624-33.

(Continued)

*Primary Examiner* — Valarie E Bertoglio
(74) *Attorney, Agent, or Firm* — Meunier Carlin & Curfman LLC

(57) ABSTRACT

Disclosed are non-naturally occurring zebrafish, such as transgenic zebrafish, which comprise a mutation in the rhodopsin (rho) gene. Also disclosed are methods of identifying compounds useful in treating retinal-specific defects and disorders, such as degeneration. Further disclosed are methods of identifying mutations in the rhodopsin gene that can cause retinal-specific defects.

9 Claims, 9 Drawing Sheets

Specification includes a Sequence Listing.

(56) References Cited

PUBLICATIONS

Chen J, Makino CL, Peachey NS, Baylor DA, Simon MI. Mechanisms of rhodopsin inactivation in vivo as revealed by a COOH-terminal truncation mutant. Science 1995; 267:374-7.

Chen J, Rattner A, Nathans J. The rod photoreceptor-specific nuclear receptor Nr2e3 represses transcription of multiple cone-specific genes. J.Neurosci. 2005; 25:118-29.

Chen, S., Oikonomou, G., Chiu, C.N., Niles, B.J., Liu, J., Lee, D.A., Antoshechkin, I., and Prober, D.A. (2013). A large-scale in vivo analysis reveals that TALENs are significantly more mutagenic than ZFNs generated using context-dependent assembly. Nucleic Acids Res. 4, 2769-2778.

Choudhury, S., Nashine, S., Bhootada, Y., Kunte, M.M., Gorbatyuk, O., Lewin, A.S., and Gorbatyuk, M. (2014). Modulation of the Rate of Retinal Degeneration in T17M RHO Mice by Reprogramming the Unfolded Protein Response. Adv. Exp. Med. Biol. 455-462.

Chuang JZ, Vega C, Jun W, Sung CH. Structural and functional impairment of endocytic pathways by retinitis pigmentosa mutant rhodopsin-arrestin complexes. J.Clin.Invest. 2004; 114:131-40.

Cideciyan, A.V., Hood, D.C., Huang, Y., Banin, E., Li, Z.Y., Stone, E.M., Milam, A.H., and Jacobson, S.G. (1998). Disease sequence from mutant rhodopsin allele to rod and cone photoreceptor degeneration in man. Proc. Natl. Acad. Sci. U. S. A. 12, 7103-7108.

Ciruna B, Weidinger G, Knaut H, Thisse B, Thisse C, Raz E, Schier AF. (2002) Production of maternal-zygotic mutant zebrafish by germ-line replacement. Proc Natl Acad Sci U S A. 99, 14919-24.

Concepcion F, Chen J. Q344ter mutation causes mislocalization of rhodopsin molecules that are catalytically active: A mouse model of Q344ter-induced retinal degeneration. PLoS One 2010; 5:e 10904.

D'Cruz PM, Yasumura D, Weir J, Matthes MT, Abderrahim H, LaVail MM, Vollrath D. Mutation of the receptor tyrosine kinase gene mertk in the retinal dystrophic RCS rat. Hum.Mol.Genet. 2000; 9:645-51.

Deretic D, Schmerl S, Hargrave PA, Arendt A, McDowell JH. Regulation of sorting and post-golgi trafficking of rhodopsin by its C-terminal sequence QVS(A)PA. Proc.Natl.Acad.Sci.U.S.A. 1998; 95:10620-5.

Drager UC, Hubei DH. Studies of visual function and its decay in mice with hereditary retinal degeneration. J.Comp.Neurol. 1978; 180:85-114.

Dryja TP, Hahn LB, Cowley GS, McGee TL, Berson EL. Mutation spectrum of the rhodopsin gene among patients with autosomal dominant retinitis pigmentosa. Proc.Natl.Acad.Sci.U.S.A. 1991; 88:9370-4.

Dryja, T.P., McGee, T.L., Hahn, L.B., Cowley, G.S., Olsson, J.E., Reichel, E., Sandberg, M.A., and Berson, E.L. (1990). Mutations within the rhodopsin gene in patients with autosomal dominant retinitis pigmentosa. N. Engl. J. Med. 19, 1302-1307.

Dryja, T.P., McGee, T.L., Reichel, E., Hahn, L.B., Cowley, G.S., Yandell, D.W., Sandberg, M.A., and Berson, E.L. (1990). A point mutation of the rhodopsin gene in one form of retinitis pigmentosa. Nature 6256, 364-366.

Easter SS,Jr, Nicola GN. The development of vision in the zebrafish (danio rerio). Dev.Biol. 1996; 180:646-63.

Fadool JM, Brockerhoff SE, Hyatt GA, Dowling JE. Mutations affecting eye morphology in the developing zebrafish (danio rerio). Dev.Genet. 1997; 20:288-95.

Fadool, J.M. (2003). Development of a rod photoreceptor mosaic revealed in transgenic zebrafish. Dev. Biol. 2, 277-290.

Fadool, J.M., and Dowling, J.E. (2008). Zebrafish: a model system for the study of eye genetics. Prog. Retin. Eye Res. 1, 89-110.

Feehan JM, Chiu CN, Stanar P, Tam BM, Ahmed SN, Moritz OL. Modeling dominant and recessive forms of retinitis pigmentosa by editing three rhodopsin-encoding genes in xenopus laevis using Crispr/Cas9. Sci.Rep. 2017; 7:6920,017-07153-4.

Fishman GA, Stone EM, Sheffield VC, Gilbert LD, Kimura AE. Ocular findings associated with rhodopsin gene codon 17 and codon 182 transition mutations in dominant retinitis pigmentosa. Arch. Ophthalmol. 1992; 110:54-62.

Frederick JM, Krasnoperova NV, Hoffmann K, Church-Kopish J, Ruther K, Howes K, Lem J, Baehr W. Mutant rhodopsin transgene expression on a null background. Invest.Ophthalmol.Vis.Sci. 2001; 42:826-33.

Gal A, Li Y, Thompson DA, Weir J, Orth U, Jacobson SG, Apfelstedt-Sylla E, Vollrath D. Mutations in MERTK, the human orthologue of the RCS rat retinal dystrophy gene, cause retinitis pigmentosa. Nat.Genet. 2000; 26:270-1.

Gorbatyuk, M.S., Knox, T., LaVail, M.M., Gorbatyuk, O.S., Noorwez, S.M., Hauswirth, W.W., Lin, J.H., Muzyczka, N., and Lewin, A.S. (2010). Restoration of visual function in P23H rhodopsin transgenic rats by gene delivery of BiP/Grp78. Proc. Natl. Acad. Sci. U. S. A. 13, 5961-5966.

Green ES, Menz MD, LaVail MM, Flannery JG. Characterization of rhodopsin mis-sorting and constitutive activation in a transgenic rat model of retinitis pigmentosa. Invest.Ophthalmol.Vis.Sci. 2000; 41:1546-53.

Gross JM, Perkins BD. Zebrafish mutants as models for congenital ocular disorders in humans. Mol.Reprod.Dev. 2008; 75:547-55.

Hargrave PA. The amino-terminal tryptic peptide of bovine rhodopsin. A glycopeptide containing two sites of oligosaccharide attachment. Biochim.Biophys.Acta 1977; 492:83-94.

Hartong DT, Berson EL, Dryja TP. Retinitis pigmentosa. Lancet 2006; 368:1795-809.

Hombrebueno JR, Tsai MM, Kim HL, De Juan J, Grzywacz NM, Lee EJ. Morphological changes of short-wavelength cones in the developing S334ter-3 transgenic rat. Brain Res. 2010; 1321:60-6.

Hu M, Easter SS. Retinal neurogenesis: The formation of the initial central patch of postmitotic cells. Dev.Biol. 1999; 207:309-21.

Huang, P., Xiao, A., Zhou, M., Zhu, Z., Lin, S., and Zhang, B. (2011). Heritable gene targeting in zebrafish using customized TALENs. Nat. Biotechnol. 8, 699-700.

Humphries MM, Rancourt D, Farrar GJ, Kenna P, Hazel M, Bush RA, Sieving PA, Sheils DM, McNally N, Creighton P, Erven A, Boros A, Gulya K, Capecchi MR, Humphries P. Retinopathy induced in mice by targeted disruption of the rhodopsin gene. NatGenet. 1997; 15:216-9.

Hwang WY, Fu Y, Reyon D, Maeder ML, Kaini P, Sander JD, Joung JK, Peterson RT, Yeh JR. Heritable and precise zebrafish genome editing using a CRISPR-cas system. PLoS One 2013; 8:e68708.

Hyatt GA, Schmitt EA, Fadool JM, Dowling JE. Retinoic acid alters photoreceptor development in vivo. Proc.Natl.Acad.Sci.U.S.A. 1996; 93:13298-303.

Ile KE, Kassen S, Cao C, Vihtehlic T, Shah SD, Mousley CJ, Alb JG,Jr, Huijbregts RP, Stearns GW, Brockerhoff SE, Hyde DR, Bankaitis VA. Zebrafish class 1 phosphatidylinositol transfer proteins: PITPbeta and double cone cell outer segment integrity in retina. Traffic 2010; 11:1151-67.

Irion U, Krauss J, Nusslein-Volhard C. Precise and efficient genome editing in zebrafish using the CRISPR/Cas9 system. Development 2014; 141:4827-30.

John SK, Smith JE, Aguirre GD, Milam AH. Loss of cone molecular markers in rhodopsin-mutant human retinas with retinitis pigmentosa. Mol.Vis. 2000; 6:204-15.

Johns PR. Growth of the adult goldfish eye. III. source of the new retinal cells. J.Comp.Neurol. 1977; 176:343-57.

Jones BW, Kondo M, Terasaki H, Watt CB, Rapp K, Anderson J, Lin Y, Shaw MV, Yang JH, Marc RE. Retinal remodeling in the tg P347L rabbit, a large-eye model of retinal degeneration. J.Comp. Neurol. 2011; 519:2713-33.

Kaushal S, Ridge KD, Khorana HG. Structure and function in rhodopsin: The role of asparagine-linked glycosylation. Proc.Natl. Acad.Sci.U.S.A. 1994; 91:4024-8.

Keeler C. Retinal degeneration in the mouse is rodless retina. J.Hered. 1966; 57:47-50.

Kijas JW, Cideciyan AV, Aleman TS, Pianta MJ, Pearce-Kelling SE, Miller BJ, Jacobson SG, Aguirre GD, Acland GM. Naturally occurring rhodopsin mutation in the dog causes retinal dysfunction and degeneration mimicking human dominant retinitis pigmentosa. Proc.Natl.Acad.Sci.U.S.A. 2002; 99:6328-33.

(56) References Cited

PUBLICATIONS

Kimura Y, Hisano Y, Kawahara A, Higashijima S. Efficient generation of knock-in transgenic zebrafish carrying reporter/driver genes by CRISPR/Cas9-mediated genome engineering. Sci.Rep. 2014; 4:6545.

Larison KD, Bremiller R. Early onset of phenotype and cell patterning in the embryonic zebrafish retina. Development 1990; 109:567-76.

Lessieur EM, Fogerty J, Gaivin RJ, Song P, Perkins BD. The ciliopathy gene ahi1 is required for zebrafish cone photoreceptor outer segment morphogenesis and survival. Invest.Ophthalmol.Vis. Sci. 2017; 58:448-60.

LaVail MM, Nishikawa S, Steinberg RH, Naash MI, Duncan JL, Trautmann N, Matthes MT, Yasumura D, Lau-Villacorta C, Chen J, Peterson WM, Yang H, Flannery JG. Phenotypic characterization of P23H and S334ter rhodopsin transgenic rat models of inherited retinal degeneration. Exp.Eye Res. 2018; 167:56-90.

Lewis TR, Kundinger SR, Pavlovich AL, Bostrom JR, Link BA, Besharse JC. Cos2/Kif7 and osm-3/Kif17 regulate onset of outer segment development in zebrafish photoreceptors through distinct mechanisms. Dev.Biol. 2017; 425:176-90.

Li T, Sandberg MA, Pawlyk BS, Rosner B, Hayes KC, Dryja TP, Berson EL. Effect of vitamin A supplementation on rhodopsin mutants threonine—17 --> methionine and proline—347 --> serine in transgenic mice and in cell cultures. Proc.Natl.Acad.Sci.U.S.A. 1998; 95:11933-8.

Malicki J, Neuhauss SC, Schier AF, Solnica-Krezel L, Stemple DL, Stainier DY, Abdelilah S, Zwartkruis F, Rangini Z, Driever W. Mutations affecting development of the zebrafish retina. Development 1996; 123:263-73.

Marc, R.E., Jones, B.W., Watt, C.B., and Strettoi, E. (2003). Neural remodeling in retinal degeneration. Prog. Retin. Eye Res. 5, 607-655.

Martinez-Navarrete G, Seiler MJ, Aramant RB, Fernandez-Sanchez L, Pinilla I, Cuenca N. Retinal degeneration in two lines of transgenic S334ter rats. Exp.Eye Res. 2011;92:227-37.

Mendes HF, van der Spuy J, Chapple JP, Cheetham ME. Mechanisms of cell death in rhodopsin retinitis pigmentosa: Implications for therapy. Trends Mol.Med. 2005; 11:177-85.

Mendes, H.F., Zaccarini, R., and Cheetham, M.E. (2010). Pharmacological manipulation of rhodopsin retinitis pigmentosa. Adv. Exp. Med. Biol. 317-323.

Montana, C.L., Kolesnikov, A.V., Shen, S.Q., Myers, C.A., Kefalov, V.J., and Corbo, J.C. (2013). Reprogramming of adult rod photoreceptors prevents retinal degeneration. Proc. Natl. Acad. Sci. U. S. A. 5, 1732-1737.

Montgomery JE, Parsons MJ, Hyde DR. A novel model of retinal ablation demonstrates that the extent of rod cell death regulates the origin of the regenerated zebrafish rod photoreceptors. J.Comp. Neurol. 2010; 518:800-14.

Moritz, O.L., and Tam, B.M. (2010). Recent insights into the mechanisms underlying light-dependent retinal degeneration from X. laevis models of retinitis pigmentosa. Adv. Exp. Med. Biol. 509-515.

Morris AC, Scholz TL, Brockerhoff SE, Fadool JM. Genetic dissection reveals two separate pathways for rod and cone regeneration in the teleost retina. Dev.Neurobiol. 2008; 68:605-19.

Morris AC, Schroeter EH, Bilotta J, Wong RO, Fadool JM. Cone survival despite rod degeneration in XOPS-mCFP transgenic zebrafish. Invest.Ophthalmol.Vis.Sci. 2005;46:4762-71.

Morrow EM, Belliveau MJ, Cepko CL. Two phases of rod photoreceptor differentiation during rat retinal development. J.Neurosci. 1998; 18:3738-48.

Morrow JM, Lazic S, Chang BS. A novel rhodopsin-like gene expressed in zebrafish retina. Vis.Neurosci. 2011; 28:325-35.

Morrow JM, Lazic S, Dixon Fox M, Kuo C, Schott RK, de A Gutierrez E, Santini F, Tropepe V, Chang BS. A second visual rhodopsin gene, rh1-2, is expressed in zebrafish photoreceptors and found in other ray-finned fishes. J.Exp.Biol. 2017; 220:294-303.

Naash MI, Hollyfield JG, al-Ubaidi MR, Baehr W. Simulation of human autosomal dominant retinitis pigmentosa in transgenic mice expressing a mutated murine opsin gene. Proc.Natl.Acad.Sci.U.S.A. 1993; 90:5499-503.

Nelson SM, Frey RA, Wardwell SL, Stenkamp DL. The developmental sequence of gene expression within the rod photoreceptor lineage in embryonic zebrafish. Dev.Dyn. 2008; 237:2903-17.

Olsson JE, Gordon JW, Pawlyk BS, Roof D, Hayes A, Molday RS, Mukai S, Cowley GS, Berson EL, Dryja TP. Transgenic mice with a rhodopsin mutation (Pro23His): A mouse model of autosomal dominant retinitis pigmentosa. Neuron 1992; 9:815-30.

Orhan E, Dalkara D, Neuille M, Lechauve C, Michiels C, Picaud S, Leveillard T, Sahel JA, Naash MI, Lavail MM, Zeitz C, Audo I. Genotypic and phenotypic characterization of P23H line 1 rat model. PLoS One 2015; 10:e0127319.

Peal, D.S., Peterson, R.T., and Milan, D. (2010). Small molecule screening in zebrafish. J. Cardiovasc. Transl. Res. 5, 454-460.

Perkins, B.D., Fadool, J.M., and Dowling, J.E. (2004). Photoreceptor structure and development: analyses using GFP transgenes. Methods Cell Biol. 315-331.

Peterson, R.T., Link, B.A., Dowling, J.E., and Schreiber, S.L. (2000). Small molecule developmental screens reveal the logic and timing of vertebrate development. Proc. Natl. Acad. Sci. U. S. A. 24, 12965-12969.

Peterson, R.T., Shaw, S.Y., Peterson, T.A., Milan, D.J., Zhong, T.P., Schreiber, S.L., MacRae, C.A., and Fishman, M.C. (2004). Chemical suppression of a genetic mutation in a zebrafish model of aortic coarctation. Nat. Biotechnol. 5, 595-599.

Petters RM, Alexander CA, Wells KD, Collins EB, Sommer JR, Blanton MR, Rojas G, Hao Y, Flowers WL, Banin E, Cideciyan AV, Jacobson SG, Wong F. Genetically engineered large animal model for studying cone photoreceptor survival and degeneration in retinitis pigmentosa. Nat.Biotechnol. 1997; 15:965-70.

Price BA, Sandoval IM, Chan F, Simons DL, Wu SM, Wensel TG, Wilson JH. Mislocalization and degradation of human P23H-rhodopsin—GFP in a knockin mouse model of retinitis pigmentosa. Invest.Ophthalmol.Vis.Sci. 2011; 52:9728-36.

Raymond PA, Barthel LK, Curran GA. Developmental patterning of rod and cone photoreceptors in embryonic zebrafish. J.Comp. Neurol. 1995; 359:537-50.

Rivolta, C., Sharon, D., DeAngelis, M.M., and Dryja, T.P. (2002). Retinitis pigmentosa and allied diseases: numerous diseases, genes, and inheritance patterns. Hum. Mol. Genet. 10, 1219-1227.

Robinson J, Schmitt EA, Dowling JE. Temporal and spatial patterns of opsin gene expression in zebrafish (danio rerio). Vis.Neurosci. 1995; 12:895-906.

Roger, J.E., Ranganath, K., Zhao, L., Cojocaru, R.I., Brooks, M., Gotoh, N., Veleri, S., Hiriyanna, A., Rachel, R.A., Campos, M.M. et al. (2012). Preservation of cone photoreceptors after a rapid yet transient degeneration and remodeling in cone-only Nrl-/- mouse retina. J. Neurosci. 2, 528-541.

Rosenfeld PJ, Cowley GS, McGee TL, Sandberg MA, Berson EL, Dryja TP. A null mutation in the rhodopsin gene causes rod photoreceptor dysfunction and autosomal recessive retinitis pigmentosa. Nat.Genet. 1992; 1:209-13.

Ross, J.W., Fernandez de Castro, J.P., Zhao, J., Samuel, M., Walters, E., Rios, C.,Bray-Ward, P., Jones, B.W., Marc, R.E., Wang, W. et al. (2012). Generation of an inbred miniature pig model of retinitis pigmentosa. Invest. Ophthalmol. Vis. Sci. 1, 501-507.

Saade CJ, Alvarez-Delfin K, Fadool JM. Rod photoreceptors protect from cone degeneration-induced retinal remodeling and restore visual responses in zebrafish. J.Neurosci. 2013; 33:1804-14.

Sakami S, Kolesnikov AV, Kefalov VJ, Palczewski K. P23H opsin knock-in mice reveal a novel step in retinal rod disc morphogenesis. Hum.Mol.Genet. 2014; 23:1723-41.

Sakami S, Maeda T, Bereta G, Okano K, Golczak M, Sumaroka A, Roman AJ, Cideciyan AV, Jacobson SG, Palczewski K. Probing mechanisms of photoreceptor degeneration in a new mouse model of the common form of autosomal dominant retinitis pigmentosa due to P23H opsin mutations. J.Biol.Chem. 2011; 286:10551-67.

(56) References Cited

PUBLICATIONS

Sander, J.D., Cade, L., Khayter, C., Reyon, D., Peterson, R.T., Joung, J.K., and Yeh, J.R. (2011). Targeted gene disruption in somatic zebrafish cells using engineered TALENs. Nat. Biotechnol. 8, 697-698.

Sandoval IM, Price BA, Gross AK, Chan F, Sammons JD, Wilson JH, Wensel TG. Abrupt onset of mutations in a developmentally regulated gene during terminal differentiation of post-mitotic photoreceptor neurons in mice. PLoS One 2014; 9:e108135.

Schmitt EA, Dowling JE. Comparison of topographical patterns of ganglion and photoreceptor cell differentiation in the retina of the zebrafish, danio rerio. J.Comp.Neurol. 1996; 371:222-34.

Schmitt EA, Dowling JE. Early retinal development in the zebrafish, danio rerio: Light and electron microscopic analyses. J.Comp. Neurol. 1999; 404:515-36.

Scott PA, de Castro JP, DeMarco PJ, Ross JW, Njoka J, Walters E, Prather RS, McCall MA, Kaplan HJ. Progression of Pro23His retinopathy in a miniature swine model of retinitis pigmentosa. Transl.Vis.Sci.Technol. 2017; 6:4.

Sotolongo-Lopez M, Alvarez-Delfin K, Saade CJ, Vera DL, Fadool JM. Genetic dissection of dual roles for the transcription factor six7 in photoreceptor development and patterning in zebrafish. PLoS Genet. 2016; 12:e1005968.

Stearns G, Evangelista M, Fadool JM, Brockerhoff SE. A mutation in the cone-specific pde6 gene causes rapid cone photoreceptor degeneration in zebrafish. J.Neurosci. 2007; 27:13866-74.

Stenkamp DL. Neurogenesis in the fish retina. Int.Rev.Cytol. 2007; 259:173-224.

Stone EM, Kimura AE, Nichols BE, Khadivi P, Fishman GA, Sheffield VC. Regional distribution of retinal degeneration in patients with the proline to histidine mutation in codon 23 of the rhodopsin gene. Ophthalmology 1991; 98:1806-13.

Sullivan LJ, Makris GS, Dickinson P, Mulhall LE, Forrest S, Cotton RG, Loughnan MS. A new codon 15 rhodopsin gene mutation in autosomal dominant retinitis pigmentosa is associated with sectorial disease. Arch.Ophthalmol. 1993; 111:1512-7.

Sullivan LS, Bowne SJ, Birch DG, Hughbanks-Wheaton D, Heckenlively JR, Lewis RA, Garcia CA, Ruiz RS, Blanton SH, Northrup H, Gire AI, Seaman R, Duzkale H, Spellicy CJ, Zhu J, Shankar SP, Daiger SP. Prevalence of disease-causing mutations in families with autosomal dominant retinitis pigmentosa: A screen of known genes in 200 families. Invest.Ophthalmol. Vis.Sci. 2006; 47:3052-64.

Sung CH, Davenport CM, Nathans J. Rhodopsin mutations responsible for autosomal dominant retinitis pigmentosa, clustering of functional classes along the polypeptide chain. J.Biol.Chem. 1993; 268:26645-9.

Sung CH, Makino C, Baylor D, Nathans J. A rhodopsin gene mutation responsible for autosomal dominant retinitis pigmentosa results in a protein that is defective in localization to the photoreceptor outer segment. J.Neurosci. 1994; 14:5818-33.

Sung CH, Schneider BG, Agarwal N, Papermaster DS, Nathans J. Functional heterogeneity of mutant rhodopsins responsible for autosomal dominant retinitis pigmentosa. Proc.Natl.Acad.Sci.U.S. A. 1991; 88:8840-4.

Tam BM, Moritz OL, Hurd LB, Papermaster DS. Identification of an outer segment targeting signal in the COOH terminus of rhodopsin using transgenic xenopus laevis. J.Cell Biol. 2000; 151:1369-80.

Tam BM, Moritz OL. Dark rearing rescues P23H rhodopsin-induced retinal degeneration in a transgenic xenopus laevis model of retinitis pigmentosa: A chromophore-dependent mechanism characterized by production of N-terminally truncated mutant rhodopsin. J.Neurosci. 2007; 27:9043-53.

Tam BM, Moritz OL. The role of rhodopsin glycosylation in protein folding, trafficking, and light-sensitive retinal degeneration. J.Neurosci. 2009; 29:15145-54.

Tam BM, Noorwez SM, Kaushal S, Kono M, Moritz OL. Photoactivation-induced instability of rhodopsin mutants T4K and T17M in rod outer segments underlies retinal degeneration in X. laevis transgenic models of retinitis pigmentosa. J.Neurosci. 2014; 34:13336-48.

Tam BM, Xie G, Oprian DD, Moritz OL. Mislocalized rhodopsin does not require activation to cause retinal degeneration and neurite outgrowth in xenopus laevis. J.Neurosci. 2006; 26:203-9.

Tam, B.M., and Moritz, O.L. (2006). Characterization of rhodopsin P23H-induced retinal degeneration in a Xenopus laevis model of retinitis pigmentosa. Invest. Ophthalmol. Vis. Sci. 8, 3234-3241.

Tamplin, O.J., White, R.M., Jing, L., Kaufman, C.K., Lacadie, S.A., Li, P., Taylor, A.M., and Zon, L.I. (2012). Small molecule screening in zebrafish: swimming in potential drug therapies. Wiley Interdiscip. Rev. Dev. Biol. 3, 459-468.

Taylor SM, Alvarez-Delfin K, Saade CJ, Thomas JL, Thummel R, Fadool JM, Hitchcock PF. The bHLH transcription factor NeuroD governs photoreceptor genesis and regeneration through delta-notch signaling. Invest.Ophthalmol.Vis.Sci. 2015;56:7496-515.

Van De Weghe JC, Rusterholz TDS, Latour B, Grout ME, Aldinger KA, Shaheen R, Dempsey JC, Maddirevula S, Cheng YH, Phelps IG, Gesemann M, Goel H, Birk OS, Alanzi T, Rawashdeh R, Khan AO, University of Washington Center for Mendelian Genomics, Bamshad MJ, Nickerson DA, Neuhauss SCF, Dobyns WB, Alkuraya FS, Roepman R, Bachmann-Gagescu R, Doherty D. Mutations in ARMC9, which encodes a basal body protein, cause joubert syndrome in humans and ciliopathy phenotypes in zebrafish. Am.J. Hum.Genet. 2017; 101:23-36.

Van Nie R, Ivanyi D, Demant P. A new H-2-linked mutation, rds, causing retinal degeneration in the mouse. Tissue Antigens 1978; 12:106-8.

Wright, A.F., Chakarova, C.F., Abd El-Aziz, M.M., and Bhattacharya, S.S. (2010). Photoreceptor degeneration: genetic and mechanistic dissection of a complex trait. Nat. Rev. Genet. 4, 273-284.

Yoshimatsu, T., Williams, P.R., D'Orazi, F.D., Suzuki, S.C., Fadool, J.M., Allison, W.T., Raymond, P.A., and Wong, R.O. (2014). Transmission from the dominant input shapes the stereotypic ratio of photoreceptor inputs onto horizontal cells. Nat. Commun. 3699.

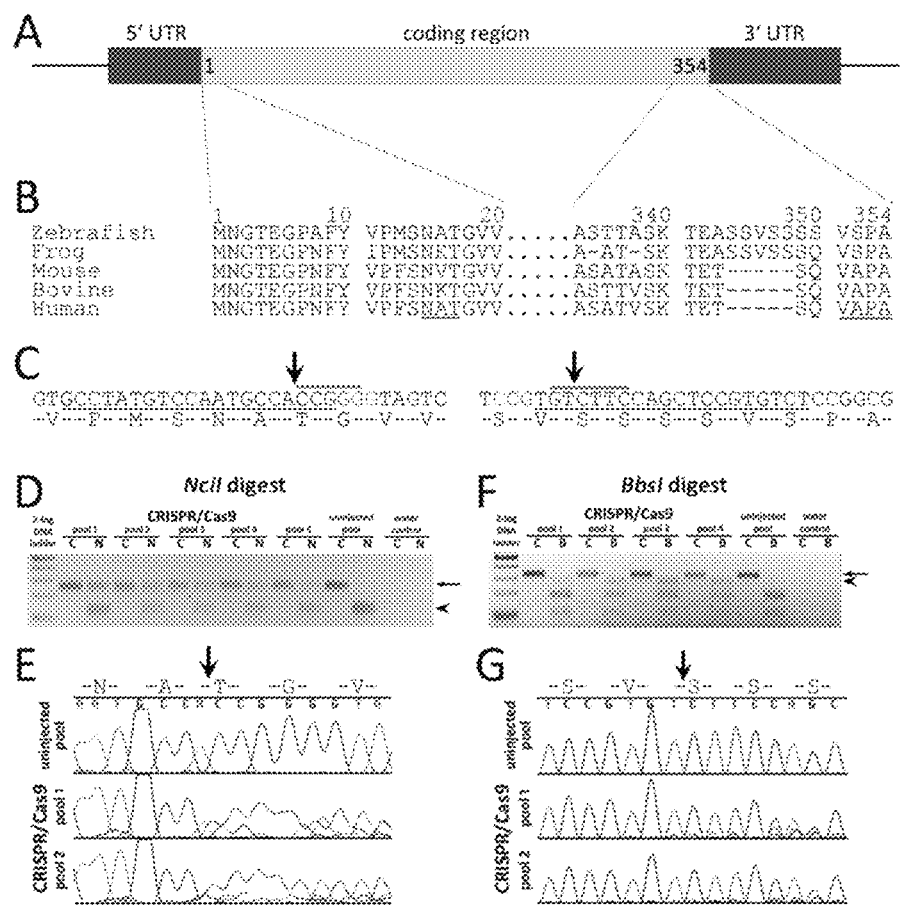
Figure 4A-G

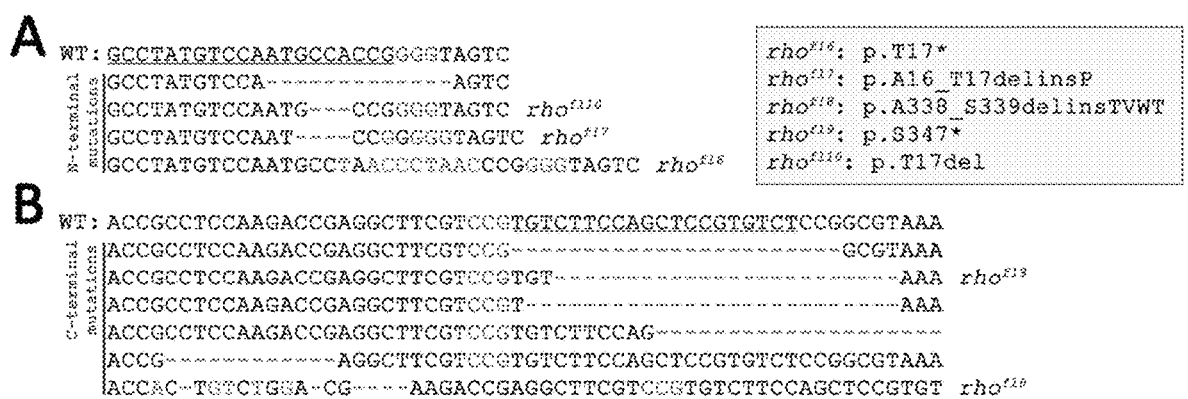
Figure 5 A-B

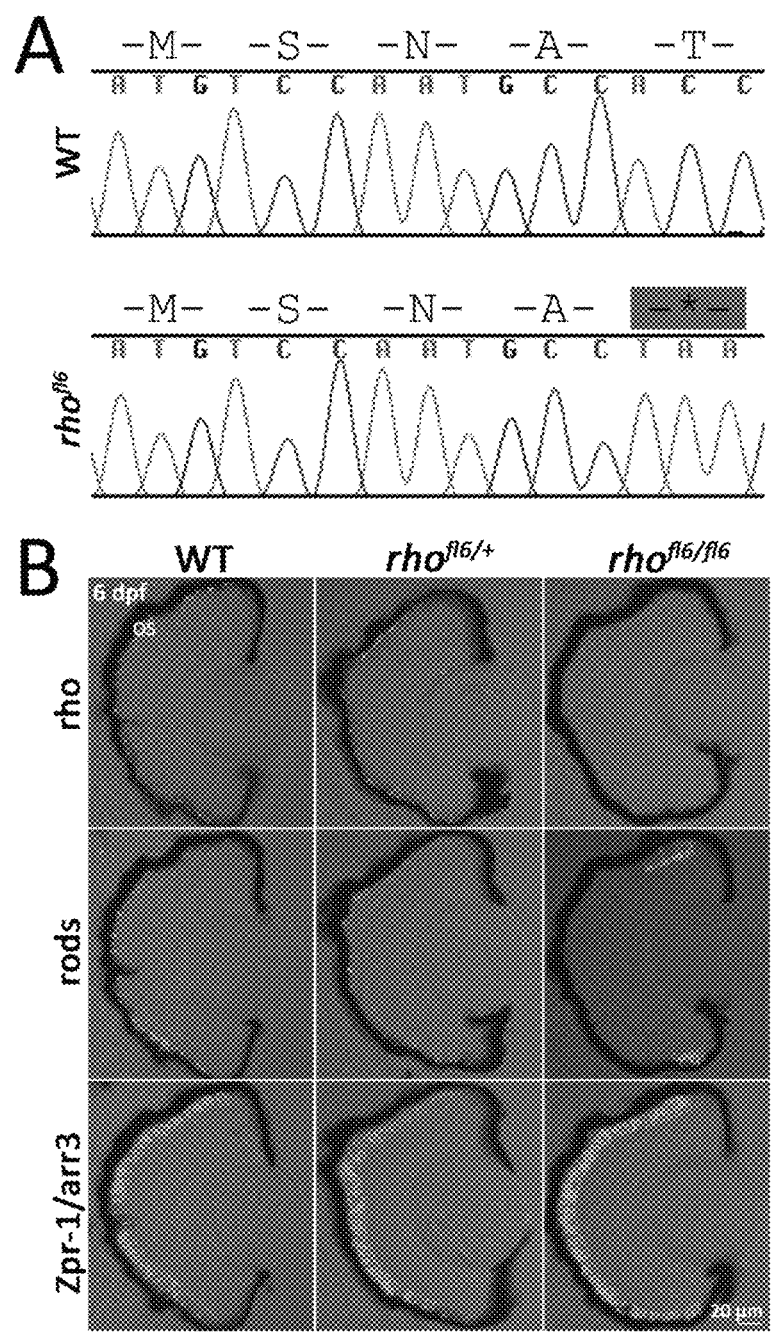
Figure 6A-B

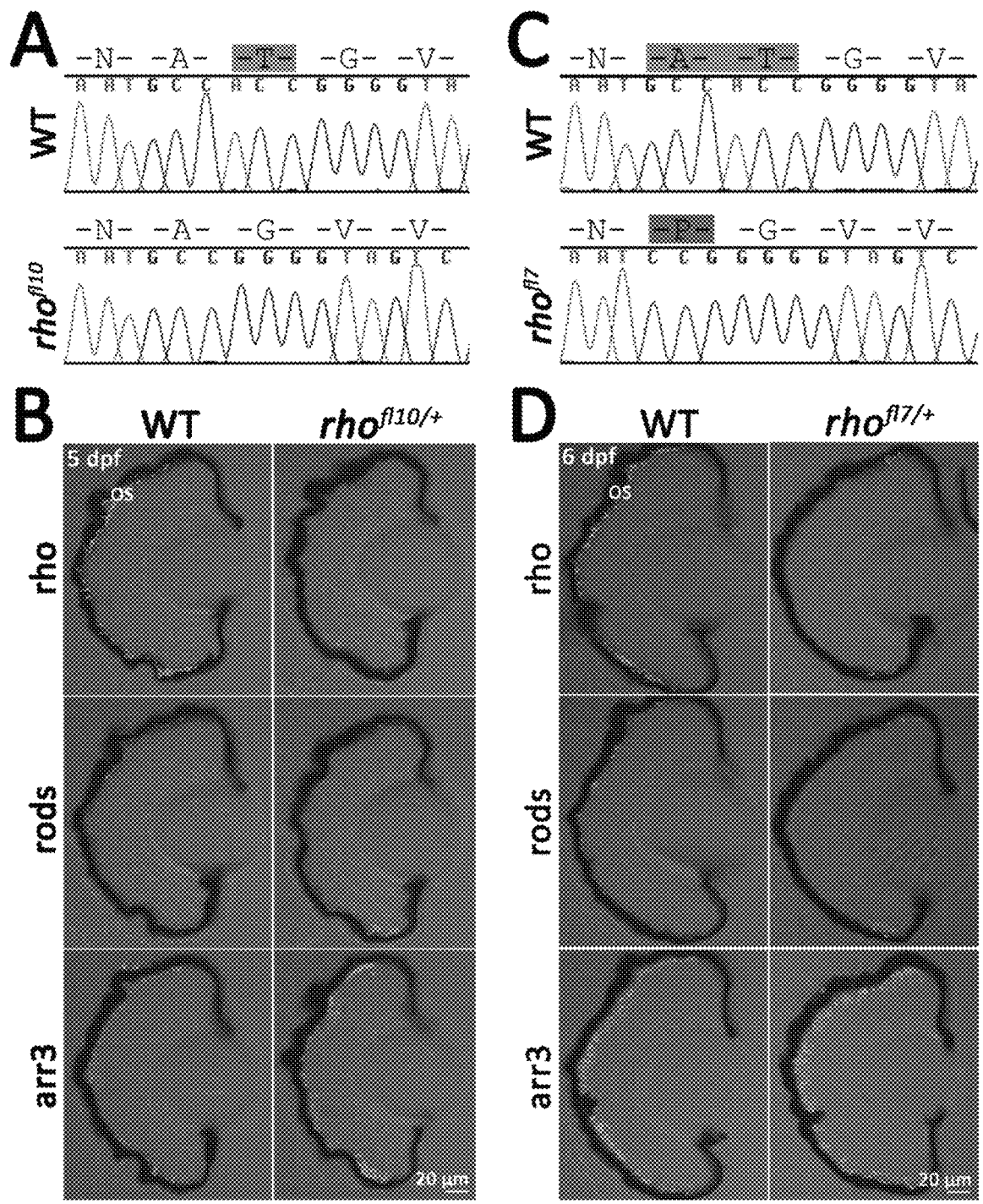
Figure 7A-D

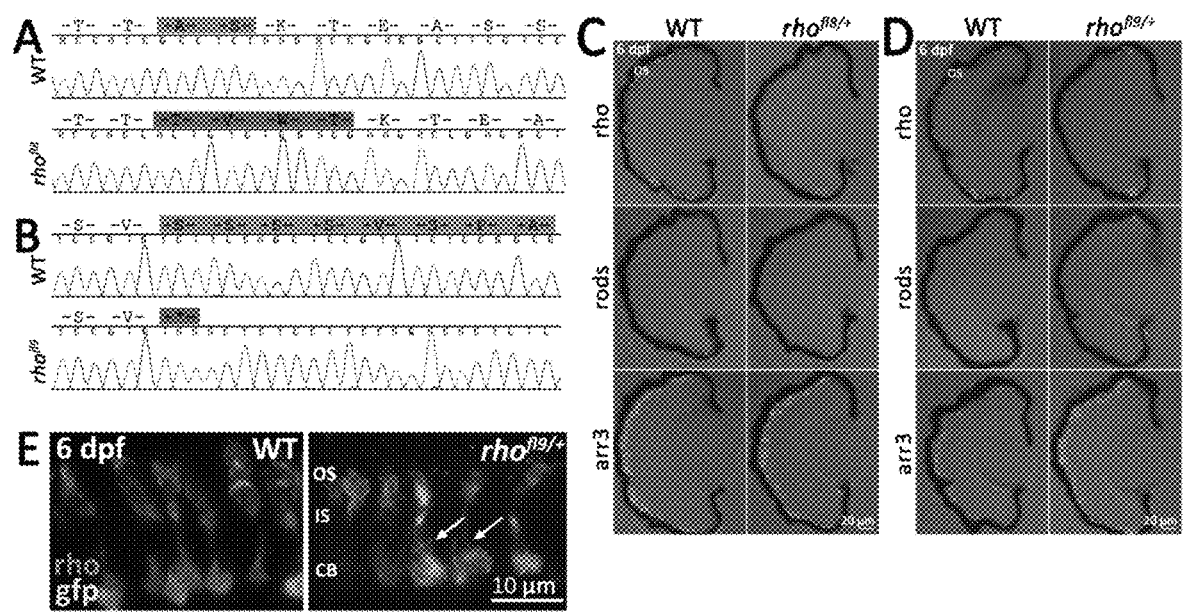
Figure 8A-E

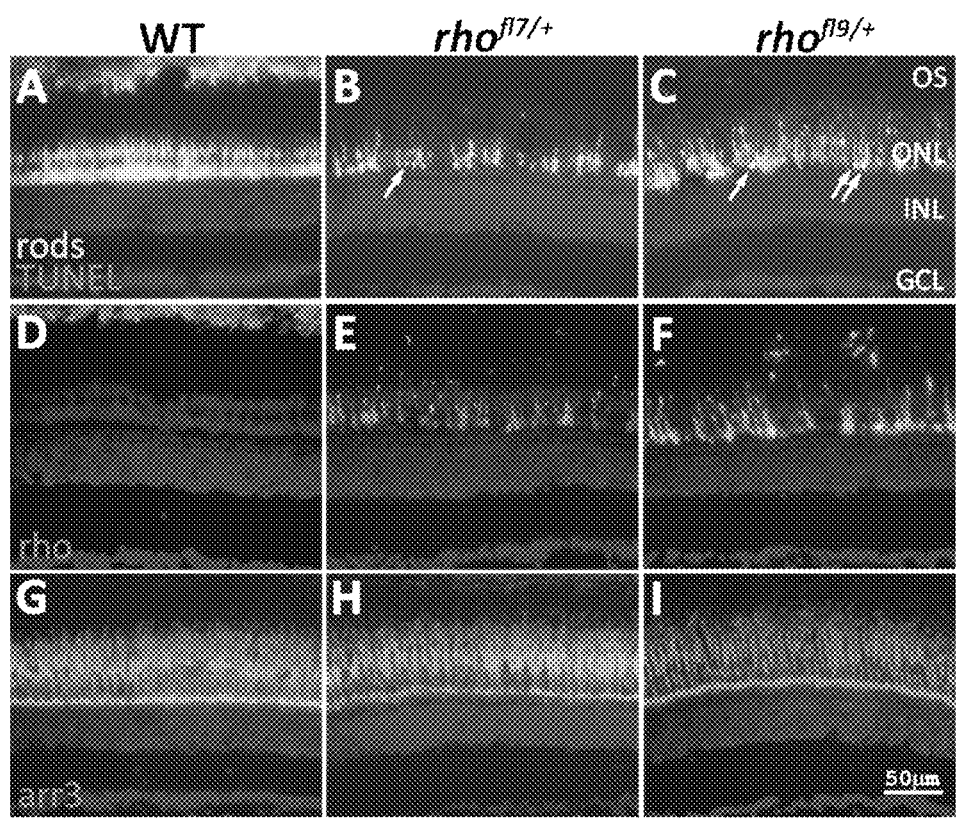
Figure 9A-I

SEQUENCE LISTING

<160> NUMBER OF SEQ ID NOS: 58

<210> SEQ ID NO 1
<211> LENGTH: 30
<212> TYPE: PRT
<213> ORGANISM: Artificial Sequence
<220> FEATURE:
<223> OTHER INFORMATION: Synthetic Construct

<400> SEQUENCE: 1

Met Asn Gly Thr Glu Gly Pro Ala Phe Tyr Val Pro Met Ser Asn Ala
1               5                   10                  15

Thr Gly Val Val Arg Ser Pro Tyr Glu Tyr Pro Gln Tyr Tyr
            20                  25                  30

<210> SEQ ID NO 2
<211> LENGTH: 29
<212> TYPE: PRT
<213> ORGANISM: Artificial Sequence
<220> FEATURE:
<223> OTHER INFORMATION: Synthetic Construct

<400> SEQUENCE: 2

Met Asn Gly Thr Glu Gly Pro Ala Phe Tyr Val Pro Met Ser Asn Thr
1               5                   10                  15

Gly Val Val Arg Ser Pro Tyr Glu Tyr Pro Gln Tyr Tyr
            20                  25

<210> SEQ ID NO 3
<211> LENGTH: 30
<212> TYPE: PRT
<213> ORGANISM: Artificial Sequence
<220> FEATURE:
<223> OTHER INFORMATION: Synthetic Construct

<400> SEQUENCE: 3

Met Asn Gly Thr Glu Gly Pro Ala Phe Tyr Val Pro Met Ser Asn Pro
1               5                   10                  15

Val Gly Val Val Arg Ser Pro Tyr Glu Tyr Pro Gln Tyr Tyr
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic Construct

<400> SEQUENCE: 4

Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic Construct

<400> SEQUENCE: 5

Met Asn Gly Thr Glu Gly Pro Asn Phe Tyr Val Pro Met Ser Asn Ala
1               5                   10                  15

Met Gly Val Val Arg Ser Pro Phe Glu Tyr Pro Gln Tyr Tyr
            20                  25                  30

<210> SEQ ID NO 6
<211> LENGTH: 30
<212> TYPE: PRT
<213> ORGANISM: Artificial Sequence
<220> FEATURE:

<223> OTHER INFORMATION: Synthetic Construct

<400> SEQUENCE: 6

Met Asn Gly Thr Glu Gly Pro Asn Phe Tyr Val Pro Met Ser Ser Ala
1               5                   10                  15

Thr Gly Val Val Arg Ser Pro Phe Glu Tyr Pro Gln Tyr Tyr
            20                  25                  30

<210> SEQ ID NO 7
<211> LENGTH: 29
<212> TYPE: PRT
<213> ORGANISM: Artificial Sequence
<220> FEATURE:
<223> OTHER INFORMATION: Synthetic Construct

<400> SEQUENCE: 7

Asn Pro Phe Glu Glu Glu Glu Gly Ala Ser Thr Thr Ala Ser Lys Thr
1               5                   10                  15

Glu Ala Ser Ser Val Ser Ser Ser Ser Val Ser Pro Ala
            20                  25

<210> SEQ ID NO 8
<211> LENGTH: 22
<212> TYPE: PRT
<213> ORGANISM: Artificial Sequence
<220> FEATURE:
<223> OTHER INFORMATION: Synthetic Construct

<400> SEQUENCE: 8

Asn Pro Phe Glu Glu Glu Glu Gly Ala Ser Thr Thr Ala Ser Lys Thr
1               5                   10                  15

Glu Ala Ser Ser Val Ser
            20

<210> SEQ ID NO 9
<211> LENGTH: 21
<212> TYPE: PRT
<213> ORGANISM: Artificial Sequence
<220> FEATURE:
<223> OTHER INFORMATION: Synthetic Construct

<400> SEQUENCE: 9

Asn Pro Phe Glu Glu Glu Glu Gly Ala Ser Thr Thr Ala Ser Lys Thr
1               5                   10                  15

Glu Ala Ser Ser Val
            20

<210> SEQ ID NO 10
<211> LENGTH: 31
<212> TYPE: PRT
<213> ORGANISM: Artificial Sequence
<220> FEATURE:
<223> OTHER INFORMATION: Synthetic Construct

<400> SEQUENCE: 10

Asn Pro Phe Glu Glu Glu Glu Gly Ala Ser Thr Thr Val Trp Thr
1               5                   10                  15

Lys Thr Glu Ala Ser Ser Val Ser Ser Ser Val Ser Pro Ala
            20                  25                  30

<210> SEQ ID NO 11
<211> LENGTH: 28
<212> TYPE: PRT
<213> ORGANISM: Artificial Sequence
<220> FEATURE:
<223> OTHER INFORMATION: Synthetic Construct

<400> SEQUENCE: 11

Ile Cys Cys Gly Lys Asn Pro Leu Gly Asp Asp Glu Ala Ser Ala Thr
1               5                   10                  15
Val Ser Lys Thr Glu Thr Ser Gln Val Ala Pro Ala
            20                  25

<210> SEQ ID NO 12
<211> LENGTH: 21
<212> TYPE: PRT
<213> ORGANISM: Artificial Sequence
<220> FEATURE:
<223> OTHER INFORMATION: Synthetic Construct

<400> SEQUENCE: 12

Ile Cys Cys Gly Lys Asn Pro Leu Gly Asp Asp Lys Thr Glu Thr Ser
1               5                   10                  15
Gln Val Ala Pro Ala
            20

<210> SEQ ID NO 13
<211> LENGTH: 27
<212> TYPE: PRT
<213> ORGANISM: Artificial Sequence
<220> FEATURE:
<223> OTHER INFORMATION: Synthetic Construct

<400> SEQUENCE: 13

Ile Cys Cys Gly Lys Asn Pro Leu Gly Asp Asp Glu Ala Ser Ala Thr
1               5                   10                  15
Val Ser Lys Glu Thr Ser Gln Val Ala Pro Ala
            20                  25

<210> SEQ ID NO 14
<211> LENGTH: 19
<212> TYPE: PRT
<213> ORGANISM: Artificial Sequence
<220> FEATURE:
<223> OTHER INFORMATION: Synthetic Construct

<400> SEQUENCE: 14

Ile Cys Cys Gly Lys Asn Pro Leu Gly Asp Asp Glu Ala Ser Ala Thr
1               5                   10                  15
Val Ser Lys

<210> SEQ ID NO 15
<211> LENGTH: 25
<212> TYPE: PRT
<213> ORGANISM: Artificial Sequence
<220> FEATURE:
<223> OTHER INFORMATION: Synthetic Construct

<400> SEQUENCE: 15

Ile Cys Cys Gly Lys Asn Pro Leu Gly Asp Asp Glu Ala Ser Ala Thr
1               5                   10                  15
Val Ser Lys Thr Gln Val Ala Pro Ala
            20                  25

<210> SEQ ID NO 16
<211> LENGTH: 30
<212> TYPE: PRT
<213> ORGANISM: Artificial Sequence
<220> FEATURE:
<223> OTHER INFORMATION: Synthetic Construct

<400> SEQUENCE: 16

Met Asn Gly Thr Glu Gly Pro Ala Phe Tyr Val Pro Met Ser Asn Ala
1               5                   10                  15

Thr Gly Val Val Arg Ser Pro Tyr Glu Tyr Pro Gln Tyr Tyr
            20                  25                  30

<210> SEQ ID NO 17
<211> LENGTH: 44
<212> TYPE: DNA
<213> ORGANISM: Artificial Sequence
<220> FEATURE:
<223> OTHER INFORMATION: Synthetic Construct

<400> SEQUENCE: 17
gccaccgggg tagtccggag cccatacgaa tacccacagt acta            44

<210> SEQ ID NO 18
<211> LENGTH: 15
<212> TYPE: PRT
<213> ORGANISM: Artificial Sequence
<220> FEATURE:
<223> OTHER INFORMATION: Synthetic Construct

<400> SEQUENCE: 18

Ala Thr Gly Val Val Arg Ser Pro Tyr Glu Tyr Pro Gln Tyr Tyr
1               5                   10                  15

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
caccgctagc taatacgact c            21

<210> SEQ ID NO 20
<211> LENGTH: 23
<212> TYPE: DNA
<213> ORGANISM: Artificial Sequence
<220> FEATURE:
<223> OTHER INFORMATION: Synthetic Construct

<400> SEQUENCE: 20
gatccgcacc gactcggtgc cac            23

<210> SEQ ID NO 21
<211> LENGTH: 23
<212> TYPE: DNA
<213> ORGANISM: Artificial Sequence
<220> FEATURE:
<223> OTHER INFORMATION: Synthetic Construct

<400> SEQUENCE: 21
gcctatgtcc aatgccaccg ggg            23

<210> SEQ ID NO 22
<211> LENGTH: 23
<212> TYPE: DNA
<213> ORGANISM: Artificial Sequence
<220> FEATURE:
<223> OTHER INFORMATION: Synthetic Construct

```
<400> SEQUENCE: 22
ccgtgtcttc cagctccgtg tct                                      23

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct

<400> SEQUENCE: 23
acagtcctgc ccagacatct a                                        21

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct

<400> SEQUENCE: 24
atggtgacgt acagcgtgag                                          20

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
gcgtggcctg gtacatcttc                                          20

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
ggtctctgtg tggtttgccg                                          20

<210> SEQ ID NO 27
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
acagtcctgc ccagacatct a                                        21

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct

<400> SEQUENCE: 28
ggtctctgtg tggtttgccg                                          20

<210> SEQ ID NO 29
```

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
atggtgacgt acagcgtgag                                                    20

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct

<400> SEQUENCE: 30
acagtcctgc ccagacatct a                                                  21

<210> SEQ ID NO 31
<211> LENGTH: 6
<212> TYPE: DNA
<213> ORGANISM: Artificial Sequence
<220> FEATURE:
<223> OTHER INFORMATION: Synthetic Construct

<400> SEQUENCE: 31 accggt                                                                    6

<210> SEQ ID NO 32
<211> LENGTH: 54
<212> TYPE: DNA
<213> ORGANISM: Artificial Sequence
<220> FEATURE:
<223> OTHER INFORMATION: Synthetic Construct

<400> SEQUENCE: 32
tctgccgatg ttcacacctg agcaggtggc ccgagtgtgc gagaatctcg agga              54

<210> SEQ ID NO 33
<211> LENGTH: 54
<212> TYPE: DNA
<213> ORGANISM: Artificial Sequence
<220> FEATURE:
<223> OTHER INFORMATION: Synthetic Construct

<400> SEQUENCE: 33
agacggctac aagtgtggac tcgtccaccg ggctcacacg ctcttagagc tcct              54

<210> SEQ ID NO 34
<211> LENGTH: 51
<212> TYPE: DNA
<213> ORGANISM: Artificial Sequence
<220> FEATURE:
<223> OTHER INFORMATION: Synthetic Construct

<400> SEQUENCE: 34
tctgccgatg ttcaccctga gcaggtggcc cgagtgtgcg agatccgagg a                 51

<210> SEQ ID NO 35
<211> LENGTH: 41
<212> TYPE: PRT
<213> ORGANISM: Artificial Sequence
<220> FEATURE:
<223> OTHER INFORMATION: Synthetic Construct

<400> SEQUENCE: 35
```

```
Met Asn Gly Thr Glu Gly Pro Ala Phe Tyr Val Pro Met Ser Asn Ala
1               5                   10                  15

Thr Gly Val Val Ala Ser Thr Ala Ser Lys Thr Glu Ala Ser Ser
                20                  25                  30

Val Ser Ser Ser Val Ser Pro Ala
        35                  40
```

<210> SEQ ID NO 36
<211> LENGTH: 39
<212> TYPE: PRT
<213> ORGANISM: Artificial Sequence
<220> FEATURE:
<223> OTHER INFORMATION: Synthetic Construct

<400> SEQUENCE: 36

```
Met Asn Gly Thr Glu Gly Pro Asn Phe Tyr Ile Pro Met Ser Asn Lys
1               5                   10                  15

Thr Gly Val Val Ala Ala Thr Ser Lys Thr Glu Ala Ser Ser Val Ser
                20                  25                  30

Ser Ser Gln Val Ser Pro Ala
        35
```

<210> SEQ ID NO 37
<211> LENGTH: 36
<212> TYPE: PRT
<213> ORGANISM: Artificial Sequence
<220> FEATURE:
<223> OTHER INFORMATION: Synthetic Construct

<400> SEQUENCE: 37

```
Met Asn Gly Thr Glu Gly Pro Asn Phe Tyr Val Pro Phe Ser Asn Val
1               5                   10                  15

Thr Gly Val Val Ala Ser Ala Thr Ala Ser Lys Thr Glu Thr Ser Gln
                20                  25                  30

Val Ala Pro Ala
        35
```

<210> SEQ ID NO 38
<211> LENGTH: 36
<212> TYPE: PRT
<213> ORGANISM: Artificial Sequence
<220> FEATURE:
<223> OTHER INFORMATION: Synthetic Construct

<400> SEQUENCE: 38

```
Met Asn Gly Thr Glu Gly Pro Asn Phe Tyr Val Pro Phe Ser Asn Lys
1               5                   10                  15

Thr Gly Val Val Ala Ser Thr Thr Val Ser Lys Thr Glu Thr Ser Gln
                20                  25                  30

Val Ala Pro Ala
        35
```

<210> SEQ ID NO 39
<211> LENGTH: 36
<212> TYPE: PRT
<213> ORGANISM: Artificial Sequence
<220> FEATURE:
<223> OTHER INFORMATION: Synthetic Construct

<400> SEQUENCE: 39

```
Met Asn Gly Thr Glu Gly Pro Asn Phe Tyr Val Pro Phe Ser Asn Ala
1               5                   10                  15
```

Thr Gly Val Val Ala Ser Ala Thr Val Ser Lys Thr Glu Thr Ser Gln
            20                  25                  30

Val Ala Pro Ala
        35

<210> SEQ ID NO 40
<211> LENGTH: 30
<212> TYPE: DNA
<213> ORGANISM: Artificial Sequence
<220> FEATURE:
<223> OTHER INFORMATION: Synthetic Construct

<400> SEQUENCE: 40
gtgcctatgt ccaatgccac cggggtagtc                                          30

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Val Pro Met Ser Asn Ala Thr Gly Val Val
1               5                   10

<210> SEQ ID NO 42
<211> LENGTH: 29
<212> TYPE: PRT
<213> ORGANISM: Artificial Sequence
<220> FEATURE:
<223> OTHER INFORMATION: Synthetic Construct

<400> SEQUENCE: 42

Thr Cys Cys Thr Gly Thr Cys Thr Thr Cys Cys Ala Gly Cys Thr Cys
1               5                   10                  15

Cys Gly Thr Gly Thr Cys Thr Cys Cys Gly Gly Cys Gly
            20                  25

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Ser Val Ser Ser Ser Ser Val Ser Pro Ala
1               5                   10

<210> SEQ ID NO 44
<211> LENGTH: 28
<212> TYPE: DNA
<213> ORGANISM: Artificial Sequence
<220> FEATURE:
<223> OTHER INFORMATION: Synthetic Construct

<400> SEQUENCE: 44
gcctatgtcc aatcggaccg gggtagtc                                            28

<210> SEQ ID NO 45
<211> LENGTH: 15
<212> TYPE: DNA
<213> ORGANISM: Artificial Sequence
<220> FEATURE:

<223> OTHER INFORMATION: Synthetic Construct

<400> SEQUENCE: 45
gcctatgtcc aagtc                                                    15

<210> SEQ ID NO 46
<211> LENGTH: 24
<212> TYPE: DNA
<213> ORGANISM: Artificial Sequence
<220> FEATURE:
<223> OTHER INFORMATION: Synthetic Construct

<400> SEQUENCE: 46
gcctatgtcc atgccggggt agtc                                          24

<210> SEQ ID NO 47
<211> LENGTH: 25
<212> TYPE: DNA
<213> ORGANISM: Artificial Sequence
<220> FEATURE:
<223> OTHER INFORMATION: Synthetic Construct

<400> SEQUENCE: 47
gcctatgtcc aatccggggg tagtc                                         25

<210> SEQ ID NO 48
<211> LENGTH: 37
<212> TYPE: DNA
<213> ORGANISM: Artificial Sequence
<220> FEATURE:
<223> OTHER INFORMATION: Synthetic Construct

<400> SEQUENCE: 48
gcctatgtcc aatgcctaac cctaacccgg ggtagtc                            37

<210> SEQ ID NO 49
<211> LENGTH: 58
<212> TYPE: DNA
<213> ORGANISM: Artificial Sequence
<220> FEATURE:
<223> OTHER INFORMATION: Synthetic Construct

<400> SEQUENCE: 49
accgcctcca agaccgaggc ttcgtccgtg tcttccagct ccgtgtctcc ggcgtaaa     58

<210> SEQ ID NO 50
<211> LENGTH: 35
<212> TYPE: DNA
<213> ORGANISM: Artificial Sequence
<220> FEATURE:
<223> OTHER INFORMATION: Synthetic Construct

<400> SEQUENCE: 50
accgcctcca agaccgaggc ttcgtccggc gtaaa                              35

<210> SEQ ID NO 51
<211> LENGTH: 34
<212> TYPE: DNA
<213> ORGANISM: Artificial Sequence
<220> FEATURE:
<223> OTHER INFORMATION: Synthetic Construct

<400> SEQUENCE: 51
accgcctcca agaccgaggc ttcgtccgtg taaa                               34

```
<210> SEQ ID NO 52
<211> LENGTH: 32
<212> TYPE: DNA
<213> ORGANISM: Artificial Sequence
<220> FEATURE:
<223> OTHER INFORMATION: Synthetic Construct

<400> SEQUENCE: 52
accgcctcca agaccgaggc ttcgtccgta aa                                   32

<210> SEQ ID NO 53
<211> LENGTH: 38
<212> TYPE: DNA
<213> ORGANISM: Artificial Sequence
<220> FEATURE:
<223> OTHER INFORMATION: Synthetic Construct

<400> SEQUENCE: 53
accgcctcca agaccgaggc ttcgtccgtg tcttccag                             38

<210> SEQ ID NO 54
<211> LENGTH: 46
<212> TYPE: DNA
<213> ORGANISM: Artificial Sequence
<220> FEATURE:
<223> OTHER INFORMATION: Synthetic Construct

<400> SEQUENCE: 54
accgaggctt cgtccgtgtc ttccagctcc gtgtctccgg cgtaaa                    46

<210> SEQ ID NO 55
<211> LENGTH: 51
<212> TYPE: DNA
<213> ORGANISM: Artificial Sequence
<220> FEATURE:
<223> OTHER INFORMATION: Synthetic Construct

<400> SEQUENCE: 55
accactgtct ggacgaagac cgaggttcgt ccgtgtcttc agctccgtg t               51

<210> SEQ ID NO 56
<211> LENGTH: 41
<212> TYPE: DNA
<213> ORGANISM: Artificial Sequence
<220> FEATURE:
<223> OTHER INFORMATION: Synthetic Construct

<400> SEQUENCE: 56
tctgccgatg ttcacacccg agtgtgcgag aatctcgagg a                         41

<210> SEQ ID NO 57
<211> LENGTH: 41
<212> TYPE: DNA
<213> ORGANISM: Artificial Sequence
<220> FEATURE:
<223> OTHER INFORMATION: Synthetic Construct

<400> SEQUENCE: 57
tctgccgatg ttcacacagg agtgtgcgag aatctagagg a                         41

<210> SEQ ID NO 58
<211> LENGTH: 41
<212> TYPE: DNA
```

```
<213> ORGANISM: Artificial Sequence
<220> FEATURE:
<223> OTHER INFORMATION: Synthetic Construct

<400> SEQUENCE: 58
tctgccgatg ttcacacctg agtgtgtgag aatctcgagg a                    41
```

MUTATIONS IN RHODOPSIN GENE IN ZEBRAFISH AND USES THEREOF

CROSS-REFERENCE TO RELATED APPLICATIONS

This application claims is a divisional application of U.S. application Ser. No. 15/972,761, filed on May 7, 2018, which claims priority to and benefit of U.S. Provisional Application No. 62/501,934, filed May 5, 2017, all of which are hereby incorporated herein by reference in their entirety.

STATEMENT REGARDING FEDERALLY FUNDED RESEARCH

This invention was made with government support under grant number EY0245410 awarded by the National Institutes of Health. The government has certain rights in the invention.

BACKGROUND

Retinitis pigmentosa (RP) represents a collection of heritable retinopathies characterized by the progressive degeneration of rod photoreceptors, followed by the secondary loss of cones and circuitry remodeling. RP is associated with mutations at over 70 loci disrupting not only phototransduction and the visual cycle but nearly every aspect of rod cell biology including development, metabolism, transport and structure. Mutations in rod opsin (RHO; OMIM 180380) are the most frequent causes of autosomal dominant (ad) RP and account for a small fraction of autosomal recessive (ar) RP (Sullivan et al. 2006). More than 150 unique mutations spanning the entire RHO coding sequence have been identified. These mutations disrupt various molecular processes including phosphorylation, glycosylation, chromophore binding, G-protein activation, arrestin-mediated endocytosis, and targeting to the rod outer segment (ROS).

The number and diversity of known mutations in RHO, led to categorization based on biochemical properties or clinical standards (Sung 1993; Sung 1991; Kaushal 1994; Chuang 2004; Cideciyan 1998; Mendes 2005). In vitro, class I mutants were defined as showing similar levels of expression to wild type RHO, reconstitute with chromophore, and fold properly, but in vivo the protein products mislocalized to the plasma membrane of the cell body (Sung 1993; Sung 1991). These mutations include several at the C-terminus which disrupt a VXPX consensus sequence which is necessary for post-Golgi trafficking and targeting of rhodopsin to the ROS (Deretic 1998). C-terminal mutations also affect conserved phosphorylation sites essential for protein-protein interactions and deactivation of RHO (Tam 2000). Class II RHO mutations exhibit reduced expression compared to wild type, poorly reconstitute with chromophore, and are retained in the trans-Golgi network, suggesting misfolded or unstable products, These mutations largely alter the 5' and membrane spanning domains, N-linked glycosylation or cysteine residues (Sung 1993). For example, T17M and RHO P23H, the most common RP allele in the United States (Chen 1995; Dryja 1991; Dryja 1990; Stone 1991), display retention in the trans-Golgi network (Sung 1993; Sung 1991; John 2000), and mutations T4K, T17M, and P23H in or near consensus glycosylation sequences (Hargrave 1977; Sullivan 1993; Fishman 1992) altered glycosylation profiles in vitro and similarly affect trafficking. Knowledge of the molecular pathology underlying rod death is incomplete, but these data and mounting evidence suggest that diverse mechanisms are responsible.

Animal models recapitulate many of the histopathological features of RP and have been invaluable for investigating the cellular and physiological consequences of disease causing mutations. Several of the earliest and frequently exploited rodent models, such as the rd1, rd2/rds, and rd10 mice (Chuang 2004; Keeler 1966; van Nie 1978; Drager 1978; Chang 2007) and the RCS rat (Bourne 1938; D'Cruz 2000; Gal 2000), harbor spontaneous mutations in genes associated with human disease. Characterization of rodent, pig, dog, and frog models over expressing mutant forms of RHO display reduced or aberrant opsin localization, thinning of the retinal outer nuclear layer (ONL), shortened or dysmorphic ROSs, rod death, and eventually cone death (Olsson 1992; Petters 1997; Tam 2006). Large animal models, such as canine, with naturally occurring mutations share common histological features with RP and have been incredible useful for pre-clinical safety testing and identifying long term expectations of novel therapies (Aguirre 2017; Aguirre 1978; Kijas 2002; Jones 2011). Consistent with the in vitro phenotype of class I mutations, such as P347L and Q344ter, in vivo opsin mislocalization precedes progressive photoreceptor death (Deretic 1998; Sung 1994; Green 2000). The S334ter transgenic rat shows opsin mislocalization at P11-13, with cone dysfunction detected at 3 weeks, and severe S-cone loss by 3 months of age (Naash 1993; LaVail 2018; Hombrenbueno 2010). The P347L transgenic pig shows ONL thinning at 2 weeks, near-complete rod degeneration by 6 weeks, but slower cone degeneration extending to 20 months (Scott 2017; Petters 1997).

Rodent models generated through knock-in of precise mutations into the endogenous Rho locus allow for the probing of very specific mechanistic hypotheses leading to RP (Sandoval 2014; Sakami 2014; Sakami 2011; Price 2011). Analysis of animals heterozygous for mutant alleles of RHO demonstrated that the relative level of expression of the mRNA and protein of the mutant alleles and those of the wild type allele are predictors of the stage of onset and severity of the degeneration phenotype (Orhan 2015). Other studies demonstrate that unlike the overexpression observed in numerous transgenic lines and in vitro, low level of expressed of P23H RHO was not associated with protein accumulation in the endoplasmic reticulum but was appropriately trafficked to the outer segment. However altered disc morphogenesis preceded degeneration (Sakami 2014; Sakami 2011). Advances in gene editing in non-mammalian species open the possibility for expanding the number of animal models harboring precise lesions of rhodopsin. A recent report took advantage of CRISPR/Cas9 to target multiple Rho loci in the tetraploid model *Xenopus laevis*. The data showed that mutation of a single locus out of three was sufficient to alter rod survival (Feehan 2017). The shared phenotypes in numerous animal models are very informative for recognizing conserved molecular mechanisms, yet the dissimilarities may contribute to understanding the variation in the onset and severity of disease observed in the clinic.

Zebrafish have proven to be a powerful forward genetic model for studying retinal development and disease (Maliki 1996; Brockerhoff 1995; Fadool 1997). The majority of the existing mutations were the product of numerous forward genetic screens to identify genes essential to embryonic development, photoreceptor function and survival (Makili 1996; Brockerhoff 1995; Fadool 1997; Alvarez-Delfin 2009). A small number of genetic mutations and transgenic zebrafish have advanced the understanding of photoreceptor degeneration induced regeneration and circuitry remodeling (Saade 2013; Morris 2005; Morris 2008; Montgomery 2010; Stearns 2007). For example, in an initial report of rapid rod death in larval Xops:mCFP transgenic zebrafish, the rod death triggered an endless stream of rod regeneration, expression of the reporter gene and another wave of cell death, yet surprisingly, the rod degeneration did not affect cone survival or function (Morris 2005). Recent advances in gene editing using TALENs and CRISPR/Cas9 have allowed gene targeting in zebrafish to test specific hypotheses of gene function in eye development (Sotolongo 2016; Lewis 2017; Taylor 2015), to generate reporter knock-ins (Auer 2014; Kimura 2014), induce precise modifications through homology-directed repair (Hwang 2013; Irion 2014; Armstrong 2016), and model human disease (Lessieur 2017; Van De Weghe 2017). Together these data show the power of genetic manipulations in zebrafish to phenocopy various human retinal diseases. There exists a critical need for models for understanding of the mechanisms leading to cell death and to accelerate development of therapies that forestall secondary defects and preserve vision.

SUMMARY

Disclosed herein is the generation, isolation and uses of zebrafish having novel genetic mutations in the endogenous zebrafish rhodopsin locus (rho) for the purpose of serving as models of human retinal disease. Rhodopsin is a protein receptor expressed in the light sensitive cells of the retina responsible for initiation of vision. Nearly 100 spontaneous mutations in the human rhodopsin gene (RHO) are associated with inherited photoreceptor degeneration, retinitis pigmentosa, progressive retinal degeneration, low vision and blindness for which there are currently no cures. The novel zebrafish models were generated in the attempt to produce known disease causing mutations in the zebrafish rho gene using in vivo CRISPR/Cas9 genome editing. DNA sequencing revealed the novelty of the isolated zebrafish mutations. Analysis of the retinal phenotypes associated with the novel alleles of zebrafish rho revealed that specific mutations were association with phenotypes that mimic the photoreceptor defects and degeneration observed in humans harboring known mutant alleles of RHO and animals models expressing mutated rhodopsin based upon the human mutations. These zebrafish models provide novel tools for investigating the cellular consequences of expression of the mutated forms of rhodopsin, and are useful for genetic, small molecules, and chemical screens, or molecular manipulations with the goals of discovering compounds, genes or treatments that may alter, slow, reverse or prevent the photoreceptor defects.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The accompanying figures, which are incorporated in and constitute a part of this specification, illustrate several aspects described below.

FIG. 4A-G shows efficient gene targeting of zebrafish rho. (A) Schematic representation of the zebrafish rho locus characterized by a single exon encoding a 354 amino acid protein and 5' and 3' UTRs. (B) Alignment of rhodopsin N- and C-terminal amino acid sequences across species. Numbering is based upon the predicted zebrafish rh1-1. The conserved N-linked glycosylation sequence and VXPX targeting sequence are underlined. (C) DNA sequence and amino acid overlay of zebrafish rh1-1 5'-(left) and 3'-(right) coding sequences. Blue text represents CRISPR PAM sequence. Underlined DNA represents target for guide RNA hybridization. Purple overscore represent restriction sites for Nci1 or Bbs1. Arrows indicate predicted Cas9 cleavage sites. (D) RFLP analysis of a 253 bp PCR product spanning the 5' rh1-1 gene (C, undigested control) and digested with Nci1 (N) shows retention of the original amplicon (arrow) from pooled DNA from injected embryos versus complete digestion of the PCR product of uninjected control DNA (arrowhead) (F) RFLP analysis of a 325 bp PCR product (C, undigested control) spanning the 3' rh1-1 sequence digested with Bbs1 (B). The PCR product (arrow) from uninjected-controls was digested to completion yielding two bands. A novel band (arrowhead) is detected in the injected embryos relative to controls (E,G) Chromatogram from Sanger sequencing of 5' and 3' rh1-1 reveals loss of resolution (E) or increased baseline noise (F) in the sequences at the predicted Cas9 cleavage site from pooled DNA from uninjected controls and 2 pool to injected-embryos. The following sequences were used for the rhodopsin alignment: *Danio rerio* (NP571159.1), *Xenopus laevis* (NP001080517.1), *Mus musculus* (NP663358.1), *Bos taurus* (NP001014890.1), *Homo sapiens* (NP000530.1) (SEQ ID NOS: 35-43 shown in Figure, respectively).

FIG. 5A-B shows alignment of rhodopsin mutations recovered in F1 generation adults. (A,B) Sequence analysis of 5' (A) and 3' (B) rho CRISPR/Cas9-induced alleles alignment to the wild type allele (WT) show the majority represent deletions and several contain insertions (red text). Blue text represents CRISPR PAM sequence. Underlined DNA represents gRNA target sequence. Alleles characterized in this report are indicated in the inset in the top right corner. (SEQ ID NOS: 44-55 shown in FIG. 5, respectively).

FIG. 6A-B shows DNA sequence and histology of rhofl6 encoding a non-sense mutation p.16T*. (A) Chromatograms overlaid with amino acid sequences comparing wild type and rhofl6 allele encoding p.16T*. (B) Confocal images of cryosections of retinas from 6 dpf wild type (WT), heterozygous rhofl6/+, or homozygous rhofl6/fl6 mutants labeled with antibodies to rho (1D1, red), rods (4C12, red), or Zpr-1/arr3a, a selective marker expressed by red/green cones (Zpr-1, red) overlaid with brightfield. Note the lack of labeling for rods in the central retina and differential labeling for rho/1D1 and rods/4C12 near the retinal margin of rhofl6/fl6 homozygous larvae suggesting that rhofl6 is a null allele.

FIG. 7A-D shows disruption of the N-linked glycosylation sequence in rhofl10 and rhofl7. (A,C) Chromatograms overlaid with amino acid sequences comparing wild type, rhofl10 and rhofl7 alleles disrupting the conserved NXT consensus glycosylation sequence at N15. Red highlights deleted amino acids; blue an insertion. (B,D) Confocal images of serial retinal cryosections of 6 dpf wild type (WT) or heterozygous rhofl10/+ and rhofl7/+ mutants labeled with antibodies to rho (1D1, red), rods (4C12, red), arr3a (Zpr-1, red) overlaid with brightfield reveal loss of rod-specific labeling in the central retina.

FIG. 8A-E shows deletion of conserved C-terminal domains in rhofl8 and rhofl9. (A, B) Chromatograms overlaid with amino acid sequences of 3' rho in wild type, rhofl8 allele and rhofl9 allele. Predicted amino acid deletions are highlighted in red on the wt sequences; insertions are highlighted in blue on the mutant sequence. (C, D) Confocal images of retinal sections of 6 dpf wild type (WT) or heterozygous rhofl8/+ or rhofl9/+ larvae labeled with antibodies to rho (1D1, red), rods (4C12, red), or arr3a (Zpr-1, red) overlaid with brightfield. (E) High magnification confocal images of 6 dpf wild type (WT) or heterozygous rhofl9/+ larvae showing rod-specific expression of EGFP (gfp, green) and immunolabeling for rho (1D1, red). In wild type retinas, the rho immunolabeling is localized to the outer segment (OS) where as in the mutant, rho immunolabeling also localized to the inner segment (IS) and the cell body (CB) (arrows).

FIG. 9A-I shows rhofl7 and rhofl9 lead to increased TUNEL in adults. Retinal sections of wild type (A, D, G) or heterozygous rhofl7/+(B, E, H) and rhofl9/+(C,F,I) adult zebrafish immunolabeled with antibodies to rods (4C12, green, A-C), rho (1D1, red, D-F), or red/green cones (arr3a/Zpr-1, red, G-I), and stained with TUNEL (red, A-C). All sections were counter stained with DAPI (blue). Immunolabeling for rods reveals fewer, less regularly arranged cells in the mutants compared to wild type (WT). TUNEL positive nuclei (arrows), positioned along the proximal region of the ONL, are only observed in the mutant retinas (A-C). In wild type retinas, rho immunolabeling is restricted to the rod outer segments (OS) at the top of the panel. Immunolabeling in rhofl7/+ and rhofl9/+ adults is localized to the cell bodies, and no outer segments are evident (D-F). Immunolabeling for red and green cones were indistinguishable across the samples (G-I). (ganglion cell layer, GCL; inner nuclear layer (INL); outer nuclear layer (ONL).

DETAILED DESCRIPTION

Definitions

Figure 1:
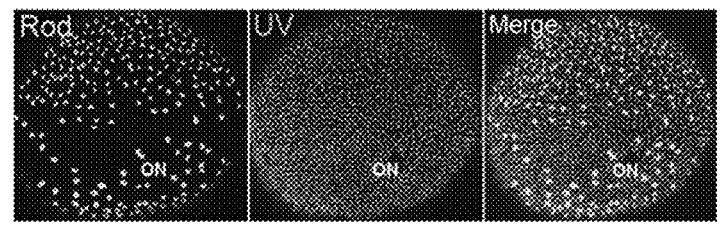
FIG. 1 shows a confocal image of a whole mount larval zebrafish retina labeled for rods and UV opsin. Dorsal is up. The images show the differences in number and spatial patterning of rods and cones from the dorsal to ventral retina. ON=optic nerve.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of .+−0.20% or .+−0.10%, more preferably .+−0.5%, even more preferably .+−0.1%, and still more preferably .+−0.0.1% from the specified value, as such variations are appropriate to perform the disclosed methods.

An "analogue," "analog" or "derivative," which are used interchangeably, refers to a compound, e.g., a peptide or polypeptide, substantially similar in structure and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, to "alleviate" a disease means to reduce the frequency or severity of at least one sign or symptom of a disease or disorder.

An "effective amount" as used herein, means an amount which provides a therapeutic or prophylactic benefit.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

As used herein, the term "cell" is herein used in its broadest sense in the art, referring to a structural unit of a tissue present in a multicellular organism, which is capable of self-replicating, has genetic information and a mechanism for expressing it, and is surrounded by a membrane structure that isolates the living body from the outside. Cells used herein may be either naturally-occurring cells or artificially modified cells (e.g., fusion cells, genetically modified cells, etc.), as long as the cell has a chemical receptor or is capable of having such a nucleic acid molecule introduced therein. Examples of cell sources include, but are not limited to, a single-cell culture; the embryo, blood, or a body tissue of a normally-grown transgenic animal, a mixture of cells derived from normally-grown cell lines, and the like. In some preferred embodiments, a cell which is easily transformed or transfected is used.

As used herein, the term "tissue" refers to an aggregate of cells having substantially the same function and/or form in a multi-cellular organism. "Tissue" is typically an aggregate of cells of the same origin, but may be an aggregate of cells of different origins as long as the cells have the same function and/or form. Typically, a tissue constitutes a part of an organ. Animal tissues are separated into epithelial tissue, connective tissue, muscular tissue, nervous tissue, and the like, on a morphological, functional, or developmental basis.

As used herein, the term "isolated" means that naturally accompanying material is at least reduced, or preferably substantially completely eliminated, in normal circumstances. Therefore, the term "isolated cell" refers to a cell substantially free from other accompanying substances (e.g., other cells, proteins, nucleic acids, etc.) in natural circumstances. The term "isolated" in relation to nucleic acids or polypeptides means that, for example, the nucleic acids or the polypeptides are substantially free from cellular substances or culture media when they are produced by recombinant DNA techniques; or precursory chemical substances or other chemical substances when they are subsequently chemically synthesized.

As used herein, the term "gene" refers to an element defining a genetic trait. A gene is typically arranged in a given sequence on a chromosome. A gene which defines the primary structure of a protein is called a structural gene. A gene which regulates the expression of a structural gene is called a regulatory gene (e.g., promoter). As used herein, "gene" may refer to a "polynucleotide", "oligonucleotide", "nucleic acid", and a "nucleic acid molecule."

As used herein, "gene product" includes a "polynucleotide", "oligonucleotide", a "nucleic acid" and a "nucleic acid molecule" and/or "protein", "polypeptide", "oligopeptide" and a "peptide", which are subsequent expression products of a gene. Those skilled in the art understand what a gene product is, according to the context used with embodiments of the present invention. Accordingly, gene used herein usually includes not only double-stranded DNA but also each single-stranded DNA, such as sense strand and antisense strand constituting thereof. Therefore, in embodiments of the present invention, the genes can include any of double-stranded DNA including human genome DNA, and single-stranded DNA (sense strand) including cDNA, as well as a single stranded DNA (antisense) having a sequence complementary to the sense strand, as well as fragments thereof.

The terms "polynucleotide", "oligonucleotide", "nucleic acid molecule" and "nucleic acid" as used herein have the same meaning and refer to a nucleotide polymer having any length. This term also includes an "oligonucleotide derivative" or a "polynucleotide derivative". An "oligonucleotide derivative" or a "polynucleotide derivative" includes a nucleotide derivative, or refers to an oligonucleotide or a polynucleotide having linkages between nucleotides different from typical linkages, which are interchangeably used.

As used herein, the term "fragment" with respect to a polypeptide or polynucleotide refers to a polypeptide or polynucleotide having a sequence length ranging from 1 to n−1 with respect to the full length of the reference polypeptide or polynucleotide (of length n). The length of the fragment can be appropriately changed depending on the purpose. For example, in the case of polypeptides, the lower limit of the length of the fragment includes 3, 4, 5, 6, 7, 8, 9, 10, 15, 20, 25, 30, 40, 50 or more nucleotides. Lengths represented by integers which are not herein specified (e.g., 1 1 and the like) can be appropriate as a lower limit. For example, in the case of polynucleotides, the lower limit of the length of the fragment includes 5, 6, 7, 8, 9, 10, 15, 20, 25, 30, 40, 50, 75, 100 or more nucleotides. Lengths represented by integers which are not herein specified (e.g., 1 1 and the like) may be appropriate as a lower limit. As used herein, the length of polypeptides or polynucleotides can be represented by the number of amino acids or nucleic acids, respectively. However, the above-described numbers are not absolute. The above-described numbers, as the upper or lower limits, are intended to include some greater or smaller numbers (e.g., .±10%), as long as the same function is maintained. In embodiments of the present invention, it is understood that any fragment can be used as long as the fragment functions as possessing transposition activity.

A "control" is an alternative subject or sample used in an experiment for comparison purpose. A control can be "positive" or "negative". For example, where the purpose of the experiment is to determine a correlation of an altered expression level of a gene with a particular type of pathology, it is generally preferable to use a positive control (a subject or a sample from a subject, carrying such alteration and exhibiting symptoms characteristic of that disease), and a negative control (a subject or a sample from a subject lacking the altered expression and clinical symptom of that disease).

"Differentially expressed" as applied to a gene, refers to the differential production of the mRNA transcribed from the gene or the protein product encoded by the gene. A differentially expressed gene may be overexpressed or underexpressed as compared to the expression level of a normal or control cell. In one aspect, it refers to a differential that is at least 1.5 times, or at least 2.5 times, or alternatively at least 5 times, or alternatively at least 10 times higher or lower than the expression level detected in a control sample. The term "differentially expressed" also refers to nucleotide sequences in a cell or tissue which are expressed where silent in a control cell or not expressed where expressed in a control cell.

As used herein, the term "modulate" means to vary the amount or intensity of an effect or outcome, e.g., to enhance, augment, diminish or reduce.

As used herein the term "ameliorate" is synonymous with "alleviate" and means to reduce or lighten. For example one may ameliorate the symptoms of sarcopenia by making them more bearable.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION OF INVENTION

Zebrafish and novel screening tools are disclosed herein, which have been used to identify genes regulating photoreceptor development and survival and their impact upon retinal circuitry (Alvarez 2009; Fadool 2003; Morris 2008; Perkins 2004; Saade 2013; Yoshimatsu 2014). The seminal investigations of rod, cone and rod/cone dystrophies in zebrafish provide compelling evidence of the highly conserved nature of the progression of disease across species. First, death of the predominant photoreceptor cell type leads to secondary death of the remaining photoreceptors. In the cone-dominated larval retina mutations in pde6c leading to degeneration of the cones are followed by secondary death of rods analogous to the fate of cones in the clinic and mammalian models of RP (Berson 2002; Cideciyan 1998). Secondly, loss of the predominant cell type results in dramatic alterations in retinal circuitry and other hallmarks of neural degenerative disease (Marc 2003; Sakami 2014; Steams 2007). Third, photoreceptor cell survival is more dependent upon the density of surviving photoreceptor than the type of surviving photoreceptor. It was first shown that in the cone-dominated zebrafish retina, cone survival and function was not dependent upon the presence of rods (Morris 2005). Furthermore, it was shown that on a cone degeneration background, genetic manipulations leading to an increased number and even distribution of rods not only enhanced rod survival, but minimized the degeneration-induced remodeling of retinal circuitry (Alvarez-Delfin 2009; Saade 2013). Rod-independent cone survival in the all cone Nrl$^{-/-}$ mouse corroborated the findings (Roger 2012). A small molecule screen using zebrafish models of RP can lead to successful identification of compounds that lessen the severity or slow the progression of the degeneration.

A large number of identified and potential loci result in vision deficit for which there are currently no cures in humans. Modeling human genetic diseases by expression of mutant rhodopsin in rodents, *Xenopus*, pig and *Drosophila* has had a significant benefit in elucidating specific cellular, physiological and biochemical alterations. Initial interest in the zebrafish centered on the advantages of the model for vertebrate development, however, it has become an increasing important model of studying mechanisms of various human diseases including those of the retina (Fadool 2003). The structure of the eye and the biochemical processes of vision are highly conserved in all vertebrates. Similarly, the effects of many drugs used in the clinic are well conserved in zebrafish. The relatively high cost and labor intensive effort associated with mammalian models limits their use in large scale chemical and gene knock-down approaches. Disclosed herein are retinal-specific defects in zebrafish that can serve in vivo models to identify novel therapeutic agents that circumvent pathological changes or stimulate compensatory mechanisms that slow the progression of retinal disease and preserve vision or identify novel targets for molecular therapy for eye disease.

Similar in design to cell culture assays, zebrafish embryos can be arrayed into microtiter plates and exposed to chemical agents by adding the dissolved compounds into the water (FIG. 1; adapted Peal 2010; Peterson 2000; Peterson 2004). Zebrafish have several clear advantages over other assays. First, cellular and tissue interactions not present in cell culture are maintained in vivo thus expanding the assay to detect alterations dependent upon tissue interactions. Second, compounds can be applied singly or in combination at any stage of development, thereby revealing the timing of drug action and minimizing potential side effects. Third, quantitative analysis of cell-specific fluorescent reporter gene expression facilitates rapid analysis of retinal phenotypes in live larvae. The accelerated pace of discovery possible with zebrafish small molecule screens is highlighted by the fact that some of the very first identified molecules are now entering clinical trials (Tamplin 2012).

Recent demonstrations of survival-promoting activity by neurotrophic agents in diverse neuronal systems have raised the possibility of pharmacological therapy for inherited and degenerative disorders of the central nervous system, in general, and the retina, in particular. The retina is the sensory epithelial surface that lines the posterior aspect of the eye, receives the image formed by the lens, transduces this image into neural signals and conveys this information to the brain by the optic nerve. The retina comprises a number of layers, principally, the ganglion cell layer, inner plexiform layer, inner nuclear layer, outer plexiform layer, outer nuclear layer, photoreceptor inner segments and outer segments. The outer nuclear layer comprises the cell bodies of the photoreceptor cells with the inner and outer segments being extensions of the cell bodies.

The photoreceptor population is composed of two subclasses of photoreceptor cells, known as rods and cones. Cones function during relatively high luminance levels and subserve high acuity day or photopic vision as well as color vision. Cone cell density peaks at the center of the retinal fovea (known as the foveola) and then drops off rapidly as a function of distance from the fovea. In contrast, rods function during relatively low light levels and subserve scotopic or night vision of relatively low acuity. Rods are absent from the center of the human fovea, first appearing at distances of 100-200 μm from the foveal center. The rod distribution is more uniform across the retina as a function of eccentricity except for a central region. While no rods are present in the foveola, the density of rods increases sharply outside the fovea with the highest rod densities being found in a broad, horizontally oriented elliptical ring at approximately the same eccentricity as the center of the optic disk. Curcio et al., "Human Photoreceptor Topography", The Journal of Comparative Neurology, 292:497-523 (1990).

Genetically Engineered Zebrafish

Disclosed herein is a non-naturally occurring zebrafish comprising one or more mutations in rhodopsin (rho) locus, wherein the mutated zebrafish exhibits a photoreceptor degeneration phenotype analogous to humans. The mutation can comprise any mutation that disrupts photoreceptors. Such mutations can be found, for example, in SEQ ID NO: 2, 3, 8, 9, 10, or 11, although any mutation that reduces or eliminates photoreceptor functionality is herein contemplated. For example, photoreceptors can be reduced by 10, 20, 30, 40, 50, 60, 70, 80, 90, or 100% (with 100% being no photoreceptor functionality). In one example, the mutation can comprise pde6c. For example, the zebrafish can be homozygous for pde6c.

The zebrafish of this invention can be a transient or a stable zebrafish. The zebrafish of this invention include zebrafish larvae, zebrafish embryos and adult zebrafish. The zebrafish in which the expression of a reporter protein is tissue-specific is contemplated for this invention.

The expression sequences used to drive expression of the reporter proteins can be isolated by one of skill in the art, for example, by screening a genomic zebrafish library for sequences upstream of the zebrafish gene of interest. The expression sequences can include a promoter, an enhancer, a silencer and necessary information processing sites, such as ribosome binding sites, RNA splice sites, polyadenylation sites and transcriptional terminator sequences.

By utilizing a non-naturally occurring zebrafish that expresses a fluorescent protein under the control of a photoreceptor-specific promoter, fluorescence can be an indicator of functionality of photoreceptors. Thus, if a zebrafish of the present invention is exposed to a compound which can cause an increase of photoreceptors, or prevent deterioration and loss of photoreceptors, such function should be readily apparent by monitoring fluorescence. Zebrafish embryos can be easily cultured in 96 well plates where they can be soaked in test compounds. The effects of the test compound can also be readily visualized. If the test compound has an effect on photoreceptors, one of skill in the art can visualize it by determining the pattern of fluorescence in the zebrafish. The compounds identified by the methods of the present invention can be utilized to treat disease states associated with rhodopsin, and retinal-specific defects in general.

As used herein, a reporter protein is any protein that can be specifically detected when expressed. Reporter proteins are useful for detecting or quantitating expression from expression sequences. For example, operatively linking nucleotide sequences encoding a reporter protein to a tissue specific expression sequence allows one to study lineage development. In such studies, the reporter protein serves as a marker for monitoring developmental processes. Many reporter proteins are known to one of skill in the art. These include, but are not limited to, β-galactosidase, luciferase, and alkaline phosphatase that produce specific detectable products. Fluorescent reporter proteins can also be used, such as green fluorescent protein (GFP), enhanced green fluorescent protein (eGFP), reef coral fluorescent protein (RCFP), cyan fluorescent protein (CFP), red fluorescent protein (RFP) and yellow fluorescent protein (YFP). For example, by utilizing GFP or RCFP, fluorescence is observed upon exposure to ultraviolet, mercury, xenon, argon or krypton arc light without the addition of a substrate. The use of reporter proteins that, like GFP, are directly detectable without requiring the addition of exogenous factors are preferred for detecting or assessing gene expression during zebrafish development. A zebrafish embryo, carrying a construct encoding a reporter protein and a tissue-specific expression sequence, such as an expression sequence that directs expression provides a rapid, real time in vivo system for analyzing spatial and temporal expression patterns.

Methods of Identifying Compounds

Also provided by the present invention is a method of identifying a compound that increases, protects, or restores photoreceptors, or is involved in correcting or preventing retinal-specific defects, comprising: a) contacting a non-naturally occurring zebrafish with a test compound, wherein the zebrafish comprises one or more mutations in rhodopsin (rho) locus and a nucleic acid encoding a reporter protein which is expressed upon activation of photoreceptors; b) detecting expression of the reporter protein in photoreceptors of zebrafish contacted with a the test compound; and c) determining whether the test compound had an effect of increasing, protecting, or restoring photoreceptors in the zebrafish. This can be done in a high throughput screen, such as a 96 well microtiter plate. Said contacting can comprise homogeneously distributing the compound in media containing a zebrafish. The contacting can also comprise injecting said compound into the zebrafish.

In order to assess the desired properties of a test compound, one can contact the zebrafish with the test compound. The effects of the test compound are assessed by observing detectable spatial and temporal changes in fluorescence, in situ hybridization signal, or immunohistochemical signal or change in visually mediated behavior. Thus, if a test compound is effective in treating or preventing eye disease, such as degeneration, upon comparison with a zebrafish not exposed to a compound, a change in localized fluorescence should be observed in the zebrafish contacted with the test compound.

In the methods of the present invention, zebrafish can be contacted with a test compound by soaking the zebrafish in the test compound or the anti-thrombotic compound for about 0.25, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, or more hours. A zebrafish of the present invention which has been soaked in a test compound can also be injected with the test compound, or alternatively injected with the test compound. One of skill in the art can also readily determine what dosages to utilize by conducting dose-dependent studies. Such dose-dependent studies are also standard in the art. In this way, one of skill in the art can determine what the "effective amount" of a particular compound is. As used herein, an "effective amount" is the amount of a compound is meant a nontoxic but sufficient amount of the compound to provide the desired effect. One of skill in the art will understand that the exact amount required will vary. However, an appropriate "effective amount" may be determined by one of ordinary skill in the art using only routine experimentation.

The compounds identified by the methods of the present invention can be utilized to treat retinal-specific defects. The compounds identified by the methods of the present invention can also be utilized in other in vitro assays. The compounds can also be utilized in other in vivo animal models of thrombosis or other disease states associated with thrombosis, such as a mouse model, a rat model, a rabbit model or a baboon model of thrombosis to study their therapeutic effect. The test compounds used in the methods described herein can be, but are not limited to, chemicals, small molecules, drugs, antibodies, peptides and secreted proteins.

Identifying Mutations Relative to Retinal-Specific Defects

Disclosed herein is a method of identifying a mutation associated with photoreceptor functionality comprising: mutagenizing a zebrafish that expresses a reporter protein in photoreceptors, and detecting a mutation in photoreceptor functionality by lack of expression of the reporter gene. For example, the rhodopsin (rho) gene can be mutagenized. This can be done randomly, or by site-directed mutagenesis, such as with TALENS or CRISPR/Cas9 (see Examples section).

Upon identification of relevant mutations, one of skill in the art would know how to compare the zebrafish sequence with other sequences in available databases in order to identify a human homologue. One of skill in the art would also be able to identify other homologues such as a mouse homologue or a rat homologue. Alternatively, sequences from the mutated zebrafish can be utilized as probes to screen a human library and identify human homologs. The zebrafish sequences can also be utilized to screen other animal libraries, such as a mouse library or a rat library. Upon identification of a mouse, rat or other animal homologue, these sequences can be utilized to screen for a human homologue, either by searching available databases, or screening a human library.

Ocular Disorders

The ocular disorders for which the present methods are intended and may be used to improve one or more parameters of vision include, but are not limited to, developmental abnormalities that affect both anterior and posterior segments of the eye. Anterior segment disorders include glaucoma, cataracts, corneal dystrophy, keratoconus. Posterior segment disorders include blinding disorders caused by photoreceptor malfunction and/or death caused by retinal dystrophies and degenerations. Retinal disorders include congenital stationary night blindness, age-related macular degeneration, congenital cone dystrophies, and a large group of retinitis-pigmentosa (RP)-related disorders. These disorders include genetically pre-disposed death of photoreceptor cells, rods and cones in the retina, occurring at various ages. Among those are severe retinopathies, such as subtypes of RP itself that progresses with age and causes blindness in childhood and early adulthood and RP-associated diseases, such as genetic subtypes of LCA, which frequently results in loss of vision during childhood, as early as the first year of life. The latter disorders are generally characterized by severe reduction, and often complete loss of photoreceptor cells, rods and cones. (Trabulsi, E I, ed., Genetic Diseases of the Eye, Oxford University Press, N Y, 1998).

In particular, this method is useful for the treatment and/or restoration of at least partial vision to subjects that have lost vision due to ocular disorders, such as RPE-associated retinopathies, which are characterized by a long-term preservation of ocular tissue structure despite loss of function and by the association between function loss and the defect or absence of a normal gene in the ocular cells of the subject. A variety of such ocular disorders are known, such as childhood onset blinding diseases, retinitis pigmentosa, macular degeneration, and diabetic retinopathy, as well as ocular blinding diseases known in the art. It is anticipated that these other disorders, as well as blinding disorders of presently unknown causation which later are characterized by the same description as above, may also be successfully treated by this method. Thus, the particular ocular disorder treated by this method may include the above-mentioned disorders and a number of diseases which have yet to be so characterized. Molecules intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like. Methods for making such formulations are well known in the art, and are described, for example, in: Remington: The Science and Practice of Pharmacy (19tn ed.), ed. A. R. Gennaro, E. W. Martin Mack Publishing Co., Easton, Pa., 1995).

A number of embodiments of the invention have been described. Nevertheless, it will be understood that various modifications may be made without departing from the spirit and scope of the invention. Accordingly, other embodiments are within the scope of the following claims.

EXAMPLES

Example 1: Gene Targeting Approaches to Generate Known Disease Causing Mutations in Zebrafish Rhodopsin as Novel Models of RP Several thousand arrayed chemicals include FDA approved compounds, kinase and phosphatase modulators, nuclear receptor agonists and antagonists, lipid precursors and numerous proprietary compounds can be screened for the potential to protect rods from cell death in several forms of retinal degeneration. Compounds that provide a protective effect or accelerate the degeneration provide a toe-hold into potential pathways for systematic manipulation.

State-of-the-art gene targeting approaches to generate known disease causing mutations in rhodopsin as novel models of RP for our drug-screening platform.

Many mutations result in similar cellular changes but the precise molecular mechanism leading to death has not been elucidated making treatment difficult. A central factor in the development of gene or chemical therapies hinges upon the availability of disease models that are fully characterized for proof-of-principle studies. Disclosed herein is a method to generate and thoroughly characterize analogous versions of rhodopsin mutations as proof-of-concept for the rapid and efficient screening for treatment strategies.

Figure 2:
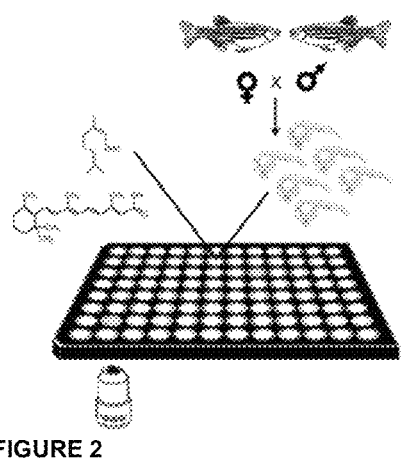
FIG. 2 shows a small molecule screen taking advantage of recovery of fluorescent reporter gene expression in zebrafish.
Figure 3:
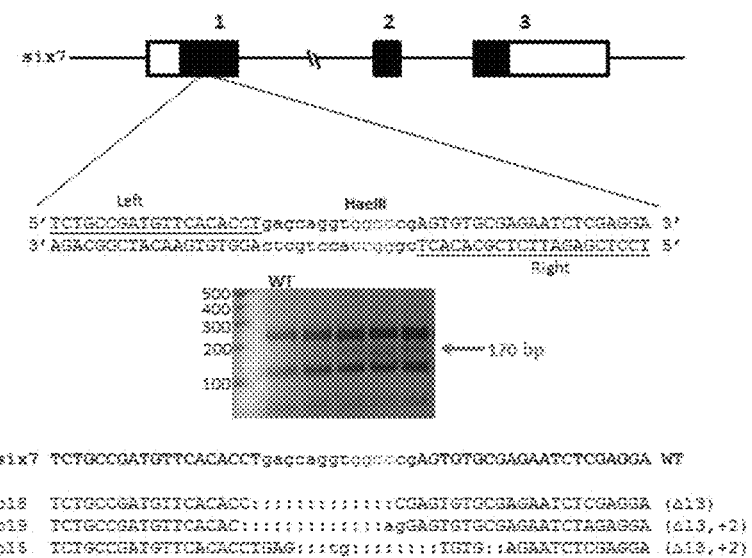
FIG. 3 shows a sequence within the first exon of six7 was targeted with left and right side TALENs (underline) flanking the spacer sequence and a HeaIII site. DNA from pools of embryos from injected animals was PCR amplified and digested with HeaIII. A new band at 170 bp corresponds to the loss of the cleavage site. DNA sequences for 3 clones show successful targeting with the disruption of the spacer sequence. (SEQ ID NOS: 32-34 and 56-58, shown respectively in the figure)

Genome editing using TALENs provides approaches to generate animal models harboring patient-specific genetic defects. In the last several years robust and reliable methods for site-specific engineering have become available in zebrafish. Thus in addition to the powerful forward genetic and transgenic approaches, gene targeting and editing are now possible. Transcription activator like-effector nucleases (TALENs), and CRISPR/Cas9 systems have been used successfully for custom engineer loci in organisms like zebrafish that show resistance to genetic manipulations by traditional techniques (Bedell 2012; Cade 2012; Chen 2012; Huang 2011; Sander 2011). Two TALENs are generated targeting neighboring DNA sequences in the gene of interest separated by a short spacer. The targeting domains are fused to FokI nuclease which functions as a dimer enabling cleavage of the double stranded DNA in a site-specific manner when both TALENs bind to their respective target sequences. Cellular repair mechanisms frequent result in small insertions or deletions (indels) disrupting the gene. In vitro transcribed mRNAs encoding the two targeting TALENs are injected into the one or two cell stage zebrafish embryo. Targeting sequences flanking a restriction site within the spacer that when mutated leads to an RFLP enables the rapid identification of fish successfully transmitting the targeted allele. The zebrafish sin oculis homologue six7 has been successfully targeted, which phenocopies the genetic and morpholino phenotypes. The strategy is shown in FIG. 2. A sequence within the first exon of six7 was targeted with left and right side TALENs (underline) flanking the spacer sequence and a HeaIII site. DNA from pools of embryos from injected animals was PCR amplified and digested with HeaIII. A new band at 170 bp corresponds to the loss of the cleavage site. DNA sequences for 3 clones show successful targeting with the disruption of the spacer sequence.

These incredibly powerful systems can be used to precisely modify targeted sequences through homology-directed repair (Bedell 2012). mRNA encoding the TALENs is co-injected with single-stranded DNA oligonucleotides homologous to the target site but encoding for the precise alteration intended. The TALEN-induced double stranded breaks may be repaired by homologous sequence using the oligo DNA as a template. Base substitutions in the oligo can facilitate introduction of novel DNA sequences or single nucleotide polymorphisms which will use to precisely engineer rho (Bedell 2012).

Disclosed herein is a method to generate two RHO alleles, encoding P23H and Q350Ter as models of Class II and I mutations respectively. Rhodopsin mutations account for 30% of autosomal dominant RP. The P23H allele of rhodopsin was the first identified and accounts for 12% of ADRP cases in North America. P23H is a prototype for Class II mutations which affects protein transport, leading to ER retention and many fail to form a chromophore (Sung 1993; Sung 1991). In contrast, Q350Ter is classified as a Class I mutation, properly sorting to the plasma membrane and generating a chromaphore, but inexplicably leading to rod death. The Rho gene located on Chromosome 8 can be targeted, which is expressed beginning at 52 hpf and through adulthood. A second Rho gene on chromosome 11 has been identified, Rhodopsin-like (Rhol), but data show that the transcript is not expressed in the larval retina, only in the adult, the expression is far lower than rho and in vitro, the protein less efficiently forms a chromophore with retinal (Morrow 2011). Shown below is the strategy for generation of the P23H allele and that for the Q350Ter allele will be the same. To generate precise lesions, a 35 base oligonucleotide homologous to the spacer sequence between and overlapping the two TALEN-targeted sequence
and including the dinucleotide polymorphism CA-AC transversions encoding the P23H mutation (bolded) is co-injected with the TALEN mRNA (3). F1 progeny of the injected animals are reared to adults and DNA is isolated from a tail clip, amplified and digested to detect the RFLP. Deletions are identified by the loss of the BspEl site (underlined). Homologous recombination are identified by the incorporation of an AgeI site ACCGGT (italicized) (SEQ ID NO: 31) with a silent base substitution for GLY upstream of the targeted codon. The region is cloned and sequence to confirm the results. Fish harboring the desired lesion are mated to generate progeny heterozygous and homozygous for the mutations.

(SEQ ID NO: 17)
5'-GCC*ACCGGT*GGGTAG<u>TCCGGA</u>GCCCATACGAATACCCACAGTACTA-3'

(SEQ ID NO: 18)
----A----T----G----V----V----R-----S-----P-----Y--

--E----Y----P----Q----Y-----Y---

The fate of the rods in the heterozygous and homozygous larvae is tested using the standard battery of histological, immunolabeling, EM and cell death assays. Larvae at various stages and adult retinas are fixed and processed. Adult scotopic and photopic vision is tested using the OKR (31). To test if the zebrafish rho P23H or Q350Ter alleles disrupt trafficking, plasmid DNA encoding a Rho C-terminal fusion to GFP under the control of the rhodopsin promoter is injected into one cell stage mutant and wildtype embryos (21), and compared to immunolabeling for rhodopsin. Larvae are examined for GFP or immunolabeling on the cell body or within the ER, common features of altered transport in photoreceptors.

This method can be used for the successful generation of multiple independent lines harboring the intended P23H and Q350Ter mutations as well as indels disrupting the rhodopsin gene. Based upon the features observed in multiple organisms, the P23H and Q350Ter mutant fish can eventually display loss of rod photoreceptors. To accelerate the degeneration, the mutations can be brought to homozygosity. Zebrafish regenerate many tissues including the retina. The null alleles of rhodopsin can be quite useful for the analysis of expression of alternative forms of rhodopsin, and the fate can be tested of rods in the absence of rhodopsin expression. If degeneration is observed in the first 6 dpf, the XOPS:GFP reporter gene can be put on the P23H and Q350Ter backgrounds for a chemical screen. These alleles can serve as models in combination with fluorescent reporter gene expression for various cellular compartments to test in vivo for subtle alterations in cellular homeostasis, organelle dysfunction and trafficking upstream of eventual gross defects and cell death.

Example 2: Screen Agents for the Ability to Increase the Survival of Rods in Two Models of Degeneration Large numbers of chemical and pharmaceutical reagents can be tested for the ability to promote rod survival in the XOPS:mCFP transgenic line or the secondary rod photoreceptor cell death following cone degeneration in pde6c mutant larvae.

In zebrafish larvae, cones outnumber rods 20:1. It has been shown that death of the cones in the pde6c mutant larvae leads to secondary death of rods making this a model to investigate secondary changes associated with photoreceptor degeneration. The demonstration that genetic manipulations that increase the number of rods protect from the secondary cell death shows the possibility of identifying compounds that confer similar protection.

Several methods can be applied to increase the efficiency of the screen and enable in vivo analysis of photoreceptor cell survival. The XOPS:GFP transgene has been placed on the pde6c mutant background to allow for tracking the spatial and temporal changes in rod survival in live animals (Fadool 2003). pde6c$^{w69}$ is a recessive allele thus only one quarter of the larvae from a mating of two heterozygotes display the mutant phenotype. To increase the efficiency of the chemical screen, genetic chimeras are generated in which the germ line of wild type animals has been eliminated and replaced by germ cells from a homozygous pde6c mutant animal (Ciruna 2002). The methods for ablation of the host germ line using morpholino knockdown, and generation of genetic chimeras by blastula cell transplant are straight forward. Following transplantation, donors are genotyped by DNA sequencing to identify homozygous mutants (Saade 2013). The host embryos that received cells from the mutant donors are reared to adults. Mating of two chimeras should produce 100% of the offspring with the mutant phenotype, which are verified by genotyping. Reports demonstrate that approximately 12% of the chimera transplants are successful (Ciruna 2002).

Adult chimeras are mated, and the embryos collected and allowed to develop for 2 days. PTU is added to the fish water to inhibit pigmentation. On the second day when photoreceptor development is initiated (Fadool 2003; Raymond 1995), five embryos are placed into a measured volume of water in each well of a 96 well tissue culture plate with black walls and a bottom composed an optically clear, thin plastic to allow unhindered fluorescence observation even with a 40× objective lens. The small molecules dissolved in DMSO at stock concentrations of 10 mM are received from the supplier arrayed in 96-well plates. A 96-pin transfer device (a small plate with 96 pins that match the spacing of the wells in the 96-well plate) is inserted into the plate containing the dissolved chemicals until the pins touch the bottoms of the wells. The pins carry a uniform volume of the chemical solutions. The device is then inserted into the plate containing zebrafish embryos, to release the chemicals from the pins. The pin transfer device is cleaned prior to the next use (Peal 2010; Peterson 2000; Peterson 2004). The embryos are allowed to grow for 2 more days in the presence of the compounds. Controls are treated with DMSO alone or are untreated. Pins of different diameter are used to transfer higher or lower volumes. The ease of treatment allows numerous samples and replicates to be performed in a single experiment.

Live larvae can be screened for persistent expression of the rod-specific GFP in at least 2 of 5 larvae at 4 and 5 days post fertilization. Samples in the 96-well plate are directly viewed with an inverted fluorescence microscope outfitted with high NA Fluar objective lenses that allow for observation of low intensity fluorescence. At 4 and 5 days of age the larvae rest on the bottom of the well facilitating rapid and reliable inspection. The microscope image can be captured using a Zeiss Axiocam digital camera. The 2.5× objective lens allows capture of the entire well in a single field of view. The presence of photoreceptor specific GFP expression is taken as evidence that the test compound protected the cells. The larvae is scored for retinal specific fluorescence on a scale of 0-3 by a standard protocol. No rescue is scored as 0, the presence of cells nearest to the margin are scored a 1, a band of cells 5-7 in width are scored a 2, and the presence of GFP expressing cells in the central retina are scored a 3. Compounds resulting in photoreceptor survival in 2 of the 5 larvae are retested at several concentrations to determine a concentration in which at least 50% of the animals show rescue. Compounds are validated by obtaining an independent lot of the agent or obtaining from a second source and their identity verified my Mass Spec.

Neuroprotective agents that slow the secondary loss of neighboring photoreceptors either through their direct action on the rods or as modifiers of the cone loss can be identified. To distinguish between these two possibilities, following validation, a separate clutch of larvae are treated and prepared for histological analysis and in situ of rod and cone morphology and gene expression using well established protocols. If survival of the cones is suspected, samples of the reagents can be subjected to independent verification and to test the ERG on drug-treated pde6c mutant and wildtype animals (Stearns 2007). At 5 dpf, the ERG is cone driven. Demonstrating a robust cone-mediate ERG confirms rescue of cones.

Small molecules can be screened to prevent the death of rods in the XOPS:mCFP transgenic line and TALEN lines. The screen for small molecule inhibitors of rod death in the well characterized XOPS:mCFP transgenic line results in rapid rod degeneration (Morris 2008; Morris 2005). Rod death in this line shows many of the features characteristic of class II RHO mutations including mis-localization of opsin, swollen ER and golgi and increased TUNEL positive cells. In addition, if the P23H and Q350Ter mutations show alteration in the first week of age, these can be run in parallel.

The P23H and Q350Ter alleles are placed on the XPOS:GFP background to facilitate screening live embryos. Lack of rod function does not affect zebrafish survival or breeding so large numbers of embryos can be collected easily from traditional mating. Embryos are arrayed into 96-well plates and treated as above. Larvae will be screened at 4 and 5 dpf.

Several secondary in vitro assays have been established. To test for direct effects upon protein processing and ER retention, HEK293 cells are transfected with Rho-GFP fusion protein expression vectors bearing Class I and Class II mutations and the effects of the drugs upon rhodopsin transport can be monitored by tracking GFP localization and immunolabeling for rhodopsin (Sung 1993; Sung 1991). Knock-down strategies that simply decrease but do not eliminate the level of expression of the toxic reporter gene protect rods from degeneration. Affects upon Rho transcription is tested in Rho promoter-luciferase reporter assays of HEK cells co-transfected with Crx and Nrl expression vectors and the level of induction of luciferase expression monitored by standard methods.

Example 3: In Vivo Gene Editing of Zebrafish Rho to Model Human Photoreceptor Disease Mutations in RHO are among the most prevalent causes of hereditary retinal degeneration. RHO alterations lead to the death of rods, and secondary loss of cones. The conservation of photoreceptor structure, gene expression and function among vertebrates has led to zebrafish rho mutations that model human photoreceptor disease. The purpose of this study was to apply in vivo genome editing to disrupt zebrafish rho.

CRISPR/Cas9 was used to induce mutations within the zebrafish rho gene. One- and two-cell staged embryos were injected with a solution containing a single guide (g) RNA targeting rho plus in vitro transcribed, capped RNA encoding Cas9. Embryos were reared for several days. Genomic DNA was isolated from injected larvae and used as the template to PCR amplify the entire coding sequence for rho. Mutations were detected with Sanger sequencing and/or restriction fragment length polymorphism. Retinal cryosections of injected and uninjected siblings were immunostained with the 1D1 monoclonal antibody which recognizes rhodopsin or 4C12, an independent rod-specific marker to verify the loss of rhodopsin expression.

rho in teleosts is characterized by a single exon with no introns. DNA sequencing of a PCR product spanning the entire rho exon showed that the larvae injected with the gRNA/Cas9 mRNA are mosaic for mutations in rho. The most common mutations are predicted to disrupt the rho coding sequence. Immunolabeling of serial sections of larvae at 6 days post fertilization showed absent or altered expression of rhodopsin in injected-larvae, however immunolabeling with an antibody to a second protein expressed by rods showed that the rod photoreceptors were present. To test for germline transmission, a subset of injected larvae were reared to adults and outcrossed. Novel rho alleles were identified in the F1 generation.

Rhodopsin Mutants

A. N-Terminal Mutations
Zebrafish Rho

|  | 10 | 20 | 30 | | |
|---|---|---|---|---|---|
| normal | MNGTEGPAFY | VPMSNATGVV | RSPYEYPQYY | (SEQ ID NO: | 1) |
| Rho p.A16del | MNGTEGPAFY | VPMSNA^GVV | RSPYEYPQYY | (SEQ ID NO: | 2) |
| Rho p.A16_T17delinsP | MNGTEGPAFY | VPMS<u>NPV</u>GVV | RSPYEYPQYY | (SEQ ID NO: | 3) |

Human RHO

```
                                        10         20         30
normal                           MNGTEGPNFY VPFSNATGVV RSPFEYPQYY   (SEQ ID NO:  4)
RHOhT17M                         MNGTEGPNFY VPMSNAMGVV RSPFEYPQYY   (SEQ ID NO:  5)
RHOhN15s                         MNGTEGPNFY VPMSSATGVV RSPFEYPQYY   (SEQ ID NO:  6)
```

B. C-Terminal Mutations
Zebrafish Rho

```
                                        330        340        350
normal                           NPFEE EEGASTTASK TEASSVSSS SVSPA   (SEQ ID NO:  7)
Rho p.S349*                      NPFEE EEGASTTASK TEASSVS*          (SEQ ID NO:  8)
Rho p.S348*                      NPFEE EEGASTTASK TEASSV*           (SEQ ID NO:  9)
Rho p.A338_K340delinsTVWTNPFEE EEGASTTTVW TKTEAS-                   (SEQ ID NO: 10)
                                 SVS SSSVSPA
Rho p.A338_T343del               NPFEE EEGASTT..^ ...EAS-           (SEQ ID NO: 10)
                                 SVS SSSVSPA
```

Human RHO

```
                                        330        340        348
                                 ICCGKNPLGD DEASATVSKT ETSQVAPA     (SEQ ID NO: 12)
RHOΔ332-38                       ICCGKNPLGD D...^...KT ETSQVAPA     (SEQ ID NO: 13)
RHOΔ340                          ICCGKNPLGD DLASATVSK^ ETSQVAPA     (SEQ ID NO: 14)
RHOΔ340-48                       ICCGKNPLGD DEASATVSK^              (SEQ ID NO: 15)
RHOΔ341-43                       ICCGKNPLGD DEASATVSKT .^.QVAPA     (SEQ ID NO: 16)
```

Diagrams depicting amino acid sequence for novel mutations of zebrafish rhodopsin (Rho) compared to published, naturally occurring mutations of human RHO. Top line is native sequence. Lower sequences are predicted amino acid changes affecting (A) the predicted N-linked glycosylation sequence (NXT; underlined), and (B) deletions (.^.) and insertion (underlined) in the C-terminus.

Example 4: Targeted Disruption of the Endogenous Zebrafish Rhodopsin Locus as Models of Rapid Rod Photoreceptor Degeneration Retinitis pigmentosa (RP) is a collection of genetic disorders that result in the degeneration of the light sensitive photoreceptor cells and blindness. RP is associated with more than 70 loci and may display dominant and recessive modes of inheritance, but mutations in the gene encoding the visual pigment rhodopsin (RHO) are the most frequent cause. Zebrafish have become a very powerful genetic model of vertebrate development and human disease including the retina. In an effort to generate precise mutations in zebrafish as novel models of photoreceptor degeneration, we describe the generation and germline transmission of a series of novel CRISPR/Cas9-induced novel insertion and deletion (indel) mutations in the major zebrafish rhodopsin locus, rh1-1. Using guide RNAs that targeted highly conserved regions of rh1-1 coupled with unbiased RFLP and DNA sequence analyses, a series of dominant and recessive alleles were recovered that resulted in the rapid degeneration of rod photoreceptors. No effect was observed upon cones. Targeting the 5'-coding sequence of rh1-1 led to the recovery of several indels similar to disease associated alleles. A frame shift mutation leading to a premature stop codon (T17*) resulted in rod degeneration when brought to homozygosity. Immunolabeling with a rhodopsin-specific antibody suggests that this is indeed a null allele suggesting that rho expression is essential for rod survival. Two in frame mutations were recovered that disrupted the highly conserved N-linked glycosylation consensus sequence at N15. Larvae heterozygous for either of the alleles demonstrated rapid rod degeneration. Targeting of the 3'-coding region of rh1-1 resulted in recovery of a premature stop codon (S347*) upstream of the conserved VSPA sorting sequence, and a second in frame allele that disrupted the putative phosphorylation site at S339. Both alleles resulted in rod death in a dominant inheritance pattern. Following loss of the targeting sequence, immunolabeling for rho was no longer restricted to the rod outer segment but also localized to the plasma membrane. The efficiency of CRISPR/Cas9 for gene targeting coupled with the large number of mutations associated RP provided a backdrop for rapid isolation of novel alleles in zebrafish that phenocopy disease. These novel lines will provide much needed in vivo models for high throughput screens of compounds or genes that protect from photoreceptor degeneration.

The purpose of this study was to generate zebrafish lines harboring mutations of the major endogenous rhodopsin locus, rh1-1, as models of rod degeneration. Using CRISPR/Cas9, we targeted conserved regions of zebrafish rh1-1 associated with photoreceptor disease in humans. Given the large number of mutations in RHO, and the ease and efficiency of gene editing using CRISPR/Cas9, we took an unbiased approach to isolate novel germline mutations of the endogenous locus and then tested for those which phenocopied the rod defects associated with similar mutations of the human locus. This approach offers a strategy for targeting zebrafish genes for functional analysis in vivo, and provides zebrafish models for investigating the initial cellular changes leading to RP with the potential to develop therapeutic treatments.

Results

CRISPR/Cas9 Targeted Mutagenesis of Zebrafish Rho

The goal was to generate lines of zebrafish harboring mutations of rh1-1 that mimic disease-causing alleles in humans. In zebrafish, rh1-1 is located on chromosome 8. As in other teleosts, the gene is represented by a single exon (FIG. 4A), but the protein sequence shares considerable homology with other vertebrate rhodopsin proteins (FIG. 4B). A second rhodopsin gene, rh1-2, is located on chromosome 11, but RNA in situ hybridization shows a spatially temporally restricted pattern of expression (Morrow 2011; Morrow 2017), therefore we focused on rh1-1. Zebrafish rh1-1 was targeted for disruption using CRISPR/Cas9 and gRNA targeting PAM sequences near conserved motifs in the 5'- and 3'-coding sequences (FIG. 4C). One- or two-cell staged zebrafish embryos microinjected with in vitro transcribed mRNA encoding Cas9 and a gRNA designed to target either the 5' rh1-1 region encoding the N-linked glycosylation consensus sequence at N15 or the 3' rh1-1 region just upstream of sequences encoding of VSPA the intracellular trafficking moiety. At 24 hours post fertilization (hpf), DNA was extracted from injected embryos and uninjected controls and used as template for PCR. The efficiency of the gRNA and Cas9 pair were analyzed by restriction fragment length polymorphism (RFLP) analysis (FIG. 4D,F) and validated by Sanger sequencing (FIG. 4E,G). Indels were detected in the 5'-coding sequence by the loss of an Nci1 restriction site and retention of the 253 bp amplicon (FIG. 4D, arrow). Alterations to the chromatograms were consistent with mosaicism in the template DNA sequence starting at the predicted Cas9 cleavage site (FIG. 4E). Indels at 3' rh1-1 were detected by the gain of a 284 bp band following digestion of a 325 bp 3'-rh1-1 amplicon with Bbs1 (FIG. 4F). Baseline noise in the chromatograms downstream of the Cas9 cleavage site was interpreted as low level of mosaicism (FIG. 4G).

To identify germline transmission of mutant rh1-1 alleles, clutches of injected embryos were grown to adults. $G_0$ adults were inbred or outcrossed to uninjected animals. DNA isolated from $F_1$ embryos was screened by RFLP and Sanger sequencing as described above. Despite relative differences observed in the alterations in the chromatograms of injected embryos, germline transmission of novel alleles affecting both targeted regions was readily identified in the $F_1$. $F_1$ progeny were grown to adults and genotyped by fin clip to identify specific rh1-1 alleles. Four mutations in the 5'-coding sequence and six mutations in the 3'-coding sequence were recovered including in-frame deletions and a putative null allele (FIG. 5). The phenotypes for 5 of the alleles are described below.

Disruption of Zebrafish N-Terminal Rho Causes Rod Degeneration

Cell-specific antibodies and transgenic reporter lines permit reliable analyses of rod and cone patterning and survival in histological sections. Differential immunolabeling with the 1D1 monoclonal antibody (mab), which recognizes rhodopsin (Hyatt 1996), and the 4C12 mab, which recognizes an epitope on the rod plasma membrane (Fadool 2003), allowed the analysis of rod survival independent of opsin expression. Of the 4 cone subtypes, red and green wavelength-sensitive cones can be immunolabeled with the Zpr-1 mab, which recognizes arr3a (Ile 2010). Sections of 6 dpf wild type larvae immunolabeled with 1D1, 4C12, or Zpr-1 were consistent with the previously described arrangement of rods and cones across the ONL. Immunolabeling with either 4C12 or 1D1/rho showed the typical asymmetric patterning of rods with the greatest intensity of labeling in the ventral retina and more sparse cells in the central and dorsal retina. 1D1 selectively labels the outer segment and 4C12 labels the entire rod photoreceptor revealing the position of their cell bodies at the innermost region of the ONL. Immunolabeling for cones shows uniform palisades across the length of the ONL (FIG. 6B). The zebrafish $rho^{f6}$ allele encodes a non-sense mutation at codon 17 (T17ter), predicted to form a truncated product or a null allele (FIG. 6A). Rod and cone distributions in heterozygous $rho^{f6/+}$ larvae appear similar to wild type. In homozygous $rho^{f6/f6}$ retinas, rho immunostaining is completely absent but immunolabeling of rods was observed close to the retinal margin, the site of continual neurogenesis in teleosts (78,79). These data are consistent with $rho^{f6/f6}$ as a likely null allele. No rod immunolabeling was observed in the central retina suggesting that rho expression in zebrafish is essential for rod survival. Labeling of red/green cones in $rho^{f6/f6}$ was indistinguishable from that of wild type, indicating that the genetic alteration resulted in a rod-specific defect.

Two of the N-terminal mutations were predicted as in-frame alterations that disrupt an N-linked glycosylation consensus sequence. N-linked glycosylation of proteins occurs at NXS/T consensus sequences, where X can be any amino acid other than proline. Human mutations at N15 and T17 disrupt a conserved glycosylation sequence and are associated with adRP. The zebrafish $rho^{f10}$ and $rho^{f7}$ alleles disrupt the conserved consensus sequence that includes N15 (FIG. 7A,C). Zebrafish $rho^{f10}$ encodes an in-frame deletion of T17 while leaving the remaining coding sequence unaltered (FIG. 7A). The zebrafish $rho^{f7}$ allele deletes both A16 and T17 and inserts a proline at codon 16 (FIG. 7C). Wild type siblings immunolabeled for rod and cone markers at 6 dpf display labeling across the ONL (FIG. 7B,D). In heterozygous $rho^{f7/+}$ and $rho^{f10/+}$ larvae, rod and rho immunolabeling are confined to the peripheral retinas, with no labeling of the central retina. Immunolabeling for cones was unaltered from the controls (FIG. 7B,D).

Disruption of Zebrafish C-Terminal Rho Causes Rod Degeneration

The C-terminal region of rho contains a conserved vectorial sorting sequence and phosphorylation sites responsible for protein-protein interactions. Several alleles were recovered using a gRNA that targeted Cas9 to a site just upstream of the DNA encoding the conserved VSPA sorting sequence. The zebrafish $rho^{f8}$ allele results in an in-frame deletion of A338 and S339 and insertion of T338, V339, W340, and T341, disrupting a putative phosphorylation site at S339 (FIG. 8A). Similar to that observed for previous alleles, immunolabeling of 6 dpf retinal sections for rho and rods was limited to a few cells near the retinal margin, whereas the red/green cones remained intact (FIG. 8C).

The zebrafish $rho^{f9}$ allele results in a non-sense mutation at codon 347 (S347ter), eliminating the final eight amino acids of the rho C-terminal tail, including the conserved VXPX targeting signal (VAPA in humans, VSPA in zebrafish) (FIG. 8D). Heterozygous $rho^{f9/+}$ larvae display loss of rods and rho staining from the central retina with no obvious effect upon immunolabeling of red/green cone photoreceptors (FIG. 7E). In humans, rodents, and frogs, disruption of the C-terminal VXPX consensus sequence results in the mistrafficking of rho to the plasma membrane. To determine if the $rho^{f9}$ mutation in zebrafish disrupts rho trafficking, the $rho^{f9}$ was placed on the Xops:EGFP reporter line background. GFP expression fills the entire rod cell body, terminals, inner segment, and to a lesser extent, the outer segment (Fadool, 2003). In wild type siblings, immunolabeling for rho specifically localizes to the outer segment. However, in $rho^{f9/+}$ heterozygous animals, immunolabeling for rho was not restricted to the outer segment, but localized to the entire cellular plasma membrane (FIG. 7F).

Rho Mislocalization and Cell Death in Adult Zebrafish with N- and C-Terminal Rho Mutations The extent of the changes in number and morphology of rods in $rho^{f7/+}$ and $rho^{f9/+}$ adult retinas were clearly evident following immunolabeling with the 4C12 mab which labels the entire rod. At this age in wild type retinas, the photoreceptor cell nuclei are tiered with rod cell bodies forming a row several cells in thickness vitread to the elongated cone nuclei (FIG. 9A). The rod inner segments project distally past the row of cone nuclei to the outer segments (FIG. 9A). In rho$^{f7/+}$ (FIG. 9B) and rho$^{f9/+}$ (FIG. 9C) retinas, fewer rods were present and their spacing and morphologies were less regular. And no outer segments were evident. In both mutant, TUNEL was observed in the ONL adjacent to the OPL (arrows, FIG. 9B,C), but none was observed in wild type retinas (FIG. 9A). Immunolabeling for rho confirmed the lack of outer segments and altered trafficking in rho$^{f7/+}$ and rho$^{f9/+}$ adult retinas. In wild type adults, immunolabeling for rho localized to the outer segments located at the most distal region of the retina (FIG. 9D, top of the panel). In heterozygous rho$^{f7/+}$ or rho$^{f9/+}$ adults, the rod cell bodies were immunolabeled for rho and little outer segment material was observed (FIG. 9E,9F). Immunolabeling for red and green cones (FIG. 9G-I), showed no differences between wild type and mutant.

Discussion

Disclosed herein is the generation and characterization of novel zebrafish models of rod degeneration generated by CRISPR/Cas9 gene disruption of two separate targets within the rh1-1 gene. Through an unbiased approach, alleles were isolated that behave like disease-causing mutations observed in the clinic, and in other well-characterized animal models. It was shown that N-terminal and C-terminal mutations result in rapid rod degeneration in larval zebrafish, however loss of rods did not appear to affect cones in adults up to 7 months of age. Ideally, targeting the endogenous zebrafish locus will recapitulate any variation in transcriptional regulation, mRNA processing of post-translational modifications which may underlay the dominant-negative, dosage-dependent or variation in onset of visual deficits observed in clinically relevant disease alleles. Ultimately, these lines in zebrafish provide much needed models for high throughput genetic and small molecule screens in an effort to identify compounds or pathways that lessen the initial pathological sequences leading to rod degeneration.

Talens and CRISPR/Cas9 have opened the door for development of a range of innovative tools and approaches to study gene function in vitro and in vivo. Where as many have taken advantage of the ability to tag genes with reporter knock-ins (Auer 2014; Kimura 2014) or induce precise modifications through homology-directed repair (Hwang 2013; Irion 2014; Armstrong 2016), a relatively simpler approach was taken to isolate novel germline mutations and retained those which phenocopied mutations of the human locus. Given the ease and efficiency of gene editing in zebrafish using CRISPR/Cas9, the extension of the approach is that gRNAs could be designed to tile any region of a gene to induce a library of in vivo mutations and then screen for effects upon gene function or novel phenotypes.

Targeted disruption of 5' rh1-1 yielded a putative null allele, rho$^{f6}$, and two alleles, rho$^{f7}$ and rho$^{f10}$, encoding in-frame mutations altering the conserved NXT glycosylation consensus sequence at N15. rho$^{f7}$ removes XT and inserts a proline, whereas rho$^{f10}$ deletes T17. In heterozygous larvae, both alleles result in rod-specific cell death and reduced opsin expression. Human mutations N15S and T17M affecting the N15 RHO glycosylation consensus sequence are associated with adRP (Sullivan 1993; Fishman 1992; Keeler 1966). RHO N15S and T17M alleles are classified as class II mutations which are expressed at lower levels than wild type opsin, fail to reconstitute with chromophore, and are retained in the trans-Golgi network in heterologous in vitro expression systems (Sung 1993; Sung 1991; Kaushal 1994). Transgenic animal models overexpressing these class II adRP alleles exhibit shortened ROSs, ONL thinning, and rod death (Tam 2009; Li 1998) confirming that glycosylation at N15 is essential.

He putative null allele, rho$^{f6}$ (T17ter) is the only mutation in the set that results in a recessive phenotype. Differential labeling was observed with a rho specific antibody and an antibody that labels an undetermined antigen expressed on the rod plasma membranes and the outer segment. Whereas most human RHO mutations cause adRP, several alleles result in arRP (Green 2000; Hartong 2006), including null alleles of RHO and G249ter, the first arRP allele identified (Rosenfeld 1992). Similar to null alleles in human and mice (Humpphries 1997), homozygous rho$^{f6}$ zebrafish exhibit rod degeneration consistent with opsin expression essential for rod survival, whereas heterozygous animal display no rod death but lower levels of immunolabeling by the rho-specific antibody. Animals homozygous for rho$^{f6}$ may provide a useful genetic background to express other mutant opsin transgenes, as previously applied in mice (Frederick 2001; Concepcion 2010).

Previous studies defined class I adRP alleles as having protein expression levels in a heterologous expression system similar to native RHO, reconstitute with retinoic acid but are mislocalized to the cellular plasma membrane. Multiple polymorphisms at each V345 and P347, as well as deletion of the distal RHO C-terminus (Q344ter) likely affect vectorial sorting of RHO to the ROS (Deretic 1998; Tam 2000). Such mutations are among the most widely-studied animal models of adRP. Zebrafish rho$^{f9}$ lacking the entire VXPX sorting signal (S347ter) exhibit opsin mislocalization, consistent with mouse, rat, rabbit, frog, and pig models (Tam 2002; Jones 2011; Sung 1994; Green 2000). In both larvae and adult zebrafish, the cones appear unaltered consistent with our previous report (Morris 2005) which has allowed for analysis of regeneration and circuitry remodeling in the absence of cone death (Saade 2013; Morris 2005; Morris 2008).

The rapid rod degeneration observed in the rh1-1 mutant zebrafish described herein compared to other animal models and human RP is a notable difference. Regardless of the lesion, mutations of the endogenous zebrafish rho result in the lack rod labeling in the central and the ventral retina by 6 dpf. Rod-specific labeling was observed near the retinal margin, the site of continuing retinal neurogenesis in teleosts (Johns 1977; Ile 2010). This pattern of cell death is similar to that observed in a transgenic line of zebrafish over expressing a membrane targeted CFP (mCFP) in rod photoreceptors (Morris 2005). Over expression of mCFP under the control of the *Xenopus* opsin promoter resulted in mislocalization rho to the plasma membrane and retention in the endoplasmic reticulum or Golgi of a Rho-GFP fusion protein (Morris 2005).

A recent report by Feehan et al. uses a similar gene targeting approach to generate endogenous mutations in the *Xenopus* rhodopsin genes and found phenotypes consistent with dominant and recessive forms of RP, including rod cell loss and opsin mislocalization. *X. laevis* are tetraploid organisms and the three rhodopsin genes examined in this study are highly conserved, with either silent or conservative amino acid differences among them. Similarly, zebrafish have a second rhodopsin-like (rho-l/rh1-2) gene stemming from a teleost genome duplication event (Morrow 2011; Morrow 2017). The rh1-2 amino acid sequence is 78% conserved with zebrafish rh1-1, with a putative N-linked glycosylation consensus sequence at N15 (NES compared with NAT in rho), but no C-terminal VXPX sorting signal. Unlike rh1-1, rh1-2 expression is absent from the retina until 5 dpf, at which time it is confined to the far peripheral retina, where it remains at 175 dpf (Morrow 2011; Morrow 2017). Data for gene targeting of rh1-2 did not reveal any rod degeneration, and death in our putative null allele of rh1-1 suggests no gene compensatory effects, consistent with late onset and limited expression pattern.

In summary, genome editing was used to generated novel alleles of the zebrafish rh1-1 locus which display inheritance patterns and molecular features similar to major classes of human alleles associated with disease. Moreover, histological analyses showed patterns of rod dysfunction and degeneration analogous to those contributing to human RP. These lines provide a useful collection of zebrafish models for use in high-throughput in vivo small molecule screen or genetic screens to identify compounds or gene targets to slow the rod degeneration associated with RP.

Materials and Methods

Animal Maintenance

AB strain zebrafish (*Danio rerio*) were reared, bred, and staged according to standard methods (Westerfield, 1995). Experiments and procedures were approved by the Florida State University Animal Care and Use Committee. The transgenic (Tg) line Tg(Xops:EGFP) expresses GFP in rods under control of the *Xenopus rhodopsin* promoter (76). Animals were anesthetized with MS222 and euthanized in ice water.

CRISPR/Cas9 Gene Editing gRNA plasmids were constructed by the Mutation Generation and Detection Core, University of Utah (http://www.cores.utah.edu/mutation-generation-detection/) to target the 5' or 3' coding region of zebrafish rho. gRNA plasmids were PCR-amplified (forward primer: 5' CACCGCTAGCTAATACGACTC 3' (SEQ ID NO: 19); reverse primer: 5' GATCCGCACCGACTCGGTGCCAC 3'; SEQ ID NO: 20) to generate 130 bp in vitro transcription templates including a T7 binding site, 20 nucleotide specificity for 5' or 3' rho, and gRNA scaffold sequence. gRNA was synthesized using the T7 MEGAshortscript kit (ThermoFisher, Waltham, Mass.; https://www.thermofisher.comAmbion/Invitrogen) followed by ethanol precipitation.

```
5' rho target sequence:
                                (SEQ ID NO: 21)
5'GCCTATGTCCAATGCCACCGGGG3'

(PAM underlined)

3' rho target sequence:
                                (SEQ ID NO: 22)
5'CCGTGTCTTCCAGCTCCGTGTCT3'

(PAM underlined)
``` pT3TS-nCas9n plasmid (Addgene #46757, Cambridge, Mass.; https://www.addgene.org/) was linearized with XbaI followed by phenol-chloroform extraction and ethanol precipitation. Linear plasmid was used as template for in vitro transcription using the mMESSAGE mMACHINE T3 kit (ThermoFisher Scientific) and RNA purified using the RNeasy Mini kit (Qiagen, Hilden, Germany; https://www.qiagen.com/us/).

A 1 nL solution containing Cas9 mRNA (200 pg/nL) and one gRNA (100 pg/nL) were microinjected into one- or two-cell staged embryos.

Screening for Mutations

DNA was extracted from 20-25 injected $G_0$ embryos or uninjected sibling controls, pooled into groups of 5 embryos, and used as template for PCR-amplification of rho. For RFLP analysis of 5' rho, a 253 bp product was amplified (forward primer: 5' ACAGTCCTGCCCAGACATCTA 3' (SEQ ID NO: 23); reverse primer: 5' ATGGTGACGTACAGCGTGAG 3') (SEQ ID NO: 24) and digested with NciI (New England Biolabs). Indels were detected by retention of the 253 bp band. For RFLP analysis of 3' rho, a 325 bp product was amplified (forward primer: 5' GCGTGGCCTGGTACATCTTC 3' (SEQ ID NO: 25); reverse primer: 5' GGTCTCTGTGTGGTTTGCCG 3', SEQ ID NO: 26) and digested with BbsI (New England Biolabs). Indels were detected with the gain of a 284 bp band. For Sanger sequencing analysis, the entire rho coding sequence was amplified (1198 bp, forward primer: 5' ACAGTCCTGCCCAGACATCTA 3' (SEQ ID NO: 27); reverse primer: 5' GGTCTCTGTGTGGTTTGCCG 3' (SEQ ID NO: 28)), purified using the EZNA Cycle Pure kit (Omega Bio-tek), and sequenced with nested primers for 5' rho

```
(5'ATGGTGACGTACAGCGTGAG3' (SEQ ID NO: 29))
or

3' rho
(5'GCGTGGCCTGGTACATCTTC3' (SEQ ID NO: 30).
```

The remaining injected $G_0$ embryos were reared to adulthood and outcrossed with wild type animals or inbred to generate $F_1$ fish. DNA was extracted from either $F_1$ embryos (typically 10-15) or from $F_1$ adult fin clip tissue and screened for mutations as described.

Histology and Imaging

Immunolabeling and fluorescence microscopy of retinal cryosections (10 μm) were performed as described previously (Fadool 2003; Fadool 2008). The following primary antibodies were used: 1D1 (mouse monoclonal, 1:20) against rhodopsin (Hyatt 1996), 4C12 (mouse monoclonal, 1:20) to label the rod plasma membrane (Fadool 2003), Zpr-1/FRet 43 (mouse monoclonal, 1:20) against arr3a to label double cone cells (Ile 2010). Species specific Alexa-conjugated secondary antibodies were from Molecular Probes (ThermoFisher). Sections were imaged using either a Zeiss Axiovert S100 fluorescent microscope or Zeiss LSM 510 Laser Confocal equipped with a 40× C-Apochromat water immersion objective (NA 1.2).

Terminal deoxynucleotide transferase (TdT)-mediated dUTP nick-end labeling (TUNEL) assay was performed on retinal cryosections using the In Situ Cell Detection kit (TMR red, Roche, Basel, Switzerland; https://www.roche.com/)) as per the manufacturer's protocol, and co-labeled for rods (4C12).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

REFERENCES

1. Sullivan L S, Bowne S J, Birch D G, Hughbanks-Wheaton D, Heckenlively J R, Lewis R A, Garcia C A, Ruiz R S, Blanton S H, Northrup H, Gire A I, Seaman R, Duzkale H, Spellicy C J, Zhu J, Shankar S P, Daiger S P. Prevalence of disease-causing mutations in families with autosomal dominant retinitis pigmentosa: A screen of known genes in 200 families. Invest. Ophthalmol. Vis. Sci. 2006; 47:3052-64.
2. Sung C H, Davenport C M, Nathans J. Rhodopsin mutations responsible for autosomal dominant retinitis pigmentosa. clustering of functional classes along the polypeptide chain. J. Biol. Chem. 1993; 268:26645-9.
3. Sung C H, Schneider B G, Agarwal N, Papermaster D S, Nathans J. Functional heterogeneity of mutant rhodopsins responsible for autosomal dominant retinitis pigmentosa. Proc. Natl. Acad. Sci. U.S.A. 1991; 88:8840-4.
4. Kaushal S, Ridge K D, Khorana H G. Structure and function in rhodopsin: The role of asparagine-linked glycosylation. Proc. Natl. Acad. Sci. U.S.A. 1994; 91:4024-8.
5. Chuang J Z, Vega C, Jun W, Sung C H. Structural and functional impairment of endocytic pathways by retinitis pigmentosa mutant rhodopsin-arrestin complexes. J. Clin. Invest. 2004; 114:131-40.
6. Cideciyan A V, Hood D C, Huang Y, Banin E, Li Z Y, Stone E M, Milam A H, Jacobson S G. Disease sequence from mutant rhodopsin allele to rod and cone photoreceptor degeneration in man. Proc. Natl. Acad. Sci. U.S.A. 1998; 95:7103-8.
7. Mendes H F, van der Spuy J, Chapple J P, Cheetham M E. Mechanisms of cell death in rhodopsin retinitis pigmentosa: Implications for therapy. Trends Mol. Med. 2005; 11:177-85.
8. Deretic D, Schmerl S, Hargrave P A, Arendt A, McDowell J H. Regulation of sorting and post-golgi trafficking of rhodopsin by its C-terminal sequence QVS(A)PA. Proc. Natl. Acad. Sci. U.S.A. 1998; 95:10620-5.
9. Tam B M, Moritz O L, Hurd L B, Papermaster D S. Identification of an outer segment targeting signal in the COOH terminus of rhodopsin using transgenic *Xenopus laevis*. J. Cell Biol. 2000; 151:1369-80.
10. Chen J, Makino C L, Peachey N S, Baylor D A, Simon M I. Mechanisms of rhodopsin inactivation in vivo as revealed by a COOH-terminal truncation mutant. Science 1995; 267:374-7.
11. Dryja T P, Hahn L B, Cowley G S, McGee T L, Berson E L. Mutation spectrum of the rhodopsin gene among patients with autosomal dominant retinitis pigmentosa. Proc. Natl. Acad. Sci. U.S.A. 1991; 88:9370-4.
12. Dryja T P, McGee T L, Hahn L B, Cowley G S, Olsson J E, Reichel E, Sandberg M A, Berson E L. Mutations within the rhodopsin gene in patients with autosomal dominant retinitis pigmentosa. N. Engl. J. Med. 1990; 323:1302-7.
13. Dryja T P, McGee T L, Reichel E, Hahn L B, Cowley G S, Yandell D W, Sandberg M A, Berson E L. A point mutation of the rhodopsin gene in one form of retinitis pigmentosa. Nature 1990; 343:364-6.
14. Stone E M, Kimura A E, Nichols B E, Khadivi P, Fishman G A, Sheffield V C. Regional distribution of retinal degeneration in patients with the proline to histidine mutation in codon 23 of the rhodopsin gene. Ophthalmology 1991; 98:1806-13.
15. John S K, Smith J E, Aguirre G D, Milam A H. Loss of cone molecular markers in rhodopsin-mutant human retinas with retinitis pigmentosa. Mol. Vis. 2000; 6:204-15.
16. Hargrave P A. The amino-terminal tryptic peptide of bovine rhodopsin. A glycopeptide containing two sites of oligosaccharide attachment. Biochim. Biophys. Acta 1977; 492:83-94.
17. Sullivan L J, Makris G S, Dickinson P, Mulhall L E, Forrest S, Cotton R G, Loughnan M S. A new codon 15 rhodopsin gene mutation in autosomal dominant retinitis pigmentosa is associated with sectorial disease. Arch. Ophthalmol. 1993; 111:1512-7.
18. Fishman G A, Stone E M, Sheffield V C, Gilbert L D, Kimura A E. Ocular findings associated with rhodopsin gene codon 17 and codon 182 transition mutations in dominant retinitis pigmentosa. Arch. Ophthalmol. 1992; 110:54-62.
19. Keeler C. Retinal degeneration in the mouse is rodless retina. J. Hered. 1966; 57:47-50.
20. van Nie R, Ivanyi D, Demant P. A new H-2-linked mutation, rds, causing retinal degeneration in the mouse. Tissue Antigens 1978; 12:106-8.
21. Drager U C, Hubel D H. Studies of visual function and its decay in mice with hereditary retinal degeneration. J. Comp. Neurol. 1978; 180:85-114.
22. Chang B, Hawes N L, Pardue M T, German A M, Hurd R E, Davisson M T, Nusinowitz S, Rengarajan K, Boyd A P, Sidney S S, Phillips M J, Stewart R E, Chaudhury R, Nickerson J M, Heckenlively J R, Boatright J H. Two mouse retinal degenerations caused by missense mutations in the beta-subunit of rod cGMP phosphodiesterase gene. Vision Res. 2007; 47:624-33.
23. Bourne M C, Campbell D A, Tansley K. Hereditary degeneration of the rat retina. Br. J. Ophthalmol. 1938; 22:613-23.
24. D'Cruz P M, Yasumura D, Weir J, Matthes M T, Abderrahim H, LaVail M M, Vollrath D. Mutation of the receptor tyrosine kinase gene mertk in the retinal dystrophic RCS rat. Hum. Mol. Genet. 2000; 9:645-51.
25. Gal A, Li Y, Thompson D A, Weir J, Orth U, Jacobson S G, Apfelstedt-Sylla E, Vollrath D. Mutations in MERTK, the human orthologue of the RCS rat retinal dystrophy gene, cause retinitis pigmentosa. Nat. Genet. 2000; 26:270-1.
26. Olsson J E, Gordon J W, Pawlyk B S, Roof D, Hayes A, Molday R S, Mukai S, Cowley G S, Berson E L, Dryja T P. Transgenic mice with a rhodopsin mutation (Pro23His): A mouse model of autosomal dominant retinitis pigmentosa. Neuron 1992; 9:815-30.
27. Petters R M, Alexander C A, Wells K D, Collins E B, Sommer J R, Blanton M R, Rojas G, Hao Y, Flowers W L, Banin E, Cideciyan A V, Jacobson S G, Wong F. Genetically engineered large animal model for studying cone photoreceptor survival and degeneration in retinitis pigmentosa. Nat. Biotechnol. 1997; 15:965-70.
28. Tam B M, Moritz O L. Characterization of rhodopsin P23H-induced retinal degeneration in a *Xenopus laevis* model of retinitis pigmentosa. Invest. Ophthalmol. Vis. Sci. 2006; 47:3234-41.
29. Tam B M, Moritz O L. Dark rearing rescues P23H rhodopsin-induced retinal degeneration in a transgenic *Xenopus laevis* model of retinitis pigmentosa: A chromophore-dependent mechanism characterized by production of N-terminally truncated mutant rhodopsin. J. Neurosci. 2007; 27:9043-53.
30. Tam B M, Moritz O L. The role of rhodopsin glycosylation in protein folding, trafficking, and light-sensitive retinal degeneration. J. Neurosci. 2009; 29:15145-54.
31. Tam B M, Noorwez S M, Kaushal S, Kono M, Moritz O L. Photoactivation-induced instability of rhodopsin mutants T4K and T17M in rod outer segments underlies retinal degeneration in *X. laevis* transgenic models of retinitis pigmentosa. J. Neurosci. 2014; 34:13336-48.

32. Tam B M, Xie G, Oprian D D, Moritz O L. Mislocalized rhodopsin does not require activation to cause retinal degeneration and neurite outgrowth in *Xenopus laevis*. J. Neurosci. 2006; 26:203-9.
33. Naash M I, Hollyfield J G, al-Ubaidi M R, Baehr W. Simulation of human autosomal dominant retinitis pigmentosa in transgenic mice expressing a mutated murine opsin gene. Proc. Natl. Acad. Sci. U.S.A. 1993; 90:5499-503.
34. Martinez-Navarrete G, Seiler M J, Aramant R B, Fernandez-Sanchez L, Pinilla I, Cuenca N. Retinal degeneration in two lines of transgenic S334ter rats. Exp. Eye Res. 2011; 92:227-37.
35. Scott P A, de Castro J P, DeMarco P J, Ross J W, Njoka J, Walters E, Prather R S, McCall M A, Kaplan H J. Progression of Pro23His retinopathy in a miniature swine model of retinitis pigmentosa. Transl. Vis. Sci. Technol. 2017; 6:4.
36. Li T, Sandberg M A, Pawlyk B S, Rosner B, Hayes K C, Dryja T P, Berson E L. Effect of vitamin A supplementation on rhodopsin mutants threonine-17→methionine and proline-347→serine in transgenic mice and in cell cultures. Proc. Natl. Acad. Sci. U.S.A. 1998; 95:11933-8.
37. Orhan E, Dalkara D, Neuille M, Lechauve C, Michiels C, Picaud S, Leveillard T, Sahel J A, Naash M I, Lavail M M, Zeitz C, Audo I. Genotypic and phenotypic characterization of P23H line 1 rat model. PLoS One 2015; 10:e0127319.
38. Aguirre G D. Concepts and strategies in retinal gene therapy. Invest. Ophthalmol. Vis. Sci. 2017; 58:5399-411.
39. Aguirre G D. Animal models as tools for screening candidate drugs. Retina 2005; 25:S36-7.
40. Aquirre G, Farber D, Lolley R, Fletcher R T, Chader G J. Rod-cone dysplasia in irish setters: A defect in cyclic GMP metabolism in visual cells. Science 1978; 201:1133-4.
41. Kijas J W, Cideciyan A V, Aleman T S, Pianta M J, Pearce-Kelling S E, Miller B J, Jacobson S G, Aguirre G D, Acland G M. Naturally occurring rhodopsin mutation in the dog causes retinal dysfunction and degeneration mimicking human dominant retinitis pigmentosa. Proc. Natl. Acad. Sci. U.S.A. 2002; 99:6328-33.
42. Jones B W, Kondo M, Terasaki H, Watt C B, Rapp K, Anderson J, Lin Y, Shaw M V, Yang J H, Marc R E. Retinal remodeling in the tg P347L rabbit, a large-eye model of retinal degeneration. J. Comp. Neurol. 2011; 519:2713-33.
43. Sung C H, Makino C, Baylor D, Nathans J. A rhodopsin gene mutation responsible for autosomal dominant retinitis pigmentosa results in a protein that is defective in localization to the photoreceptor outer segment. J. Neurosci. 1994; 14:5818-33.
44. Green E S, Menz M D, LaVail M M, Flannery J G. Characterization of rhodopsin mis-sorting and constitutive activation in a transgenic rat model of retinitis pigmentosa. Invest. Ophthalmol. Vis. Sci. 2000; 41:1546-53.
45. LaVail M M, Nishikawa S, Steinberg R H, Naash M I, Duncan J L, Trautmann N, Matthes M T, Yasumura D, Lau-Villacorta C, Chen J, Peterson W M, Yang H, Flannery J G. Phenotypic characterization of P23H and S334ter rhodopsin transgenic rat models of inherited retinal degeneration. Exp. Eye Res. 2018; 167:56-90.
46. Hombrebueno J R, Tsai M M, Kim H L, De Juan J, Grzywacz N M, Lee E J. Morphological changes of short-wavelength cones in the developing S334ter-3 transgenic rat. Brain Res. 2010; 1321:60-6.
47. Sandoval I M, Price B A, Gross A K, Chan F, Sammons J D, Wilson J H, Wensel T G. Abrupt onset of mutations in a developmentally regulated gene during terminal differentiation of postmitotic photoreceptor neurons in mice. PLoS One 2014; 9:e108135.
48. Sakami S, Kolesnikov A V, Kefalov V J, Palczewski K. P23H opsin knock-in mice reveal a novel step in retinal rod disc morphogenesis. Hum. Mol. Genet. 2014; 23:1723-41.
49. Sakami S, Maeda T, Bereta G, Okano K, Golczak M, Sumaroka A, Roman A J, Cideciyan A V, Jacobson S G, Palczewski K. Probing mechanisms of photoreceptor degeneration in a new mouse model of the common form of autosomal dominant retinitis pigmentosa due to P23H opsin mutations. J. Biol. Chem. 2011; 286:10551-67.
50. Price B A, Sandoval I M, Chan F, Simons D L, Wu S M, Wensel T G, Wilson J H. Mislocalization and degradation of human P23H-rhodopsin-GFP in a knockin mouse model of retinitis pigmentosa. Invest. Ophthalmol. Vis. Sci. 2011; 52:9728-36.
51. Feehan J M, Chiu C N, Stanar P, Tam B M, Ahmed S N, Moritz O L. Modeling dominant and recessive forms of retinitis pigmentosa by editing three rhodopsin-encoding genes in *Xenopus laevis* using Crispr/Cas9. Sci. Rep. 2017; 7:6920, 017-07153-4.
52. Malicki J, Neuhauss S C, Schier A F, Solnica-Krezel L, Stemple D L, Stainier D Y, Abdelilah S, Zwartkruis F, Rangini Z, Driever W. Mutations affecting development of the zebrafish retina. Development 1996; 123:263-73.
53. Brockerhoff S E, Hurley J B, Janssen-Bienhold U, Neuhauss S C, Driever W, Dowling J E. A behavioral screen for isolating zebrafish mutants with visual system defects. Proc. Natl. Acad. Sci. U.S.A. 1995; 92:10545-9.
54. Fadool J M, Brockerhoff S E, Hyatt G A, Dowling J E. Mutations affecting eye morphology in the developing zebrafish (*Danio rerio*). Dev. Genet. 1997; 20:288-95.
55. Fadool J M, Dowling J E. Zebrafish: A model system for the study of eye genetics. Prog. Retin. Eye Res. 2008; 27:89-110.
56. Gross J M, Perkins B D. Zebrafish mutants as models for congenital ocular disorders in humans. Mol. Reprod. Dev. 2008; 75:547-55.
57. Alvarez-Delfin K, Morris A C, Snelson C D, Gamse J T, Gupta T, Marlow F L, Mullins M C, Burgess H A, Granato M, Fadool J M. Tbx2b is required for ultraviolet photoreceptor cell specification during zebrafish retinal development. Proc. Natl. Acad. Sci. U.S.A. 2009; 106:2023-8.
58. Saade C J, Alvarez-Delfin K, Fadool J M. Rod photoreceptors protect from cone degeneration-induced retinal remodeling and restore visual responses in zebrafish. J. Neurosci. 2013; 33:1804-14.
59. Morris A C, Schroeter E H, Bilotta J, Wong R O, Fadool J M. Cone survival despite rod degeneration in XOPS-mCFP transgenic zebrafish. Invest. Ophthalmol. Vis. Sci. 2005; 46:4762-71.
60. Morris A C, Scholz T L, Brockerhoff S E, Fadool J M. Genetic dissection reveals two separate pathways for rod and cone regeneration in the teleost retina. Dev. Neurobiol. 2008; 68:605-19.
61. Montgomery J E, Parsons M J, Hyde D R. A novel model of retinal ablation demonstrates that the extent of rod cell death regulates the origin of the regenerated zebrafish rod photoreceptors. J. Comp. Neurol. 2010; 518:800-14.
62. Stearns G, Evangelista M, Fadool J M, Brockerhoff S E. A mutation in the cone-specific pde6 gene causes rapid cone photoreceptor degeneration in zebrafish. J. Neurosci. 2007; 27:13866-74.

63. Sotolongo-Lopez M, Alvarez-Delfin K, Saade C J, Vera D L, Fadool J M. Genetic dissection of dual roles for the transcription factor six7 in photoreceptor development and patterning in zebrafish. PLoS Genet. 2016; 12:e1005968.
64. Lewis T R, Kundinger S R, Pavlovich A L, Bostrom J R, Link B A, Besharse J C. Cos 2/Kif7 and osm-3/Kif17 regulate onset of outer segment development in zebrafish photoreceptors through distinct mechanisms. Dev. Biol. 2017; 425:176-90.
65. Taylor S M, Alvarez-Delfin K, Saade C J, Thomas J L, Thummel R, Fadool J M, Hitchcock P F. The bHLH transcription factor NeuroD governs photoreceptor genesis and regeneration through delta-notch signaling. Invest. Ophthalmol. Vis. Sci. 2015; 56:7496-515.
66. Auer T O, Duroure K, De Cian A, Concordet J P, Del Bene F. Highly efficient CRISPR/Cas9-mediated knock-in in zebrafish by homology-independent DNA repair. Genome Res. 2014; 24:142-53.
67. Kimura Y, Hisano Y, Kawahara A, Higashijima S. Efficient generation of knock-in transgenic zebrafish carrying reporter/driver genes by CRISPR/Cas9-mediated genome engineering. Sci. Rep. 2014; 4:6545.
68. Hwang W Y, Fu Y, Reyon D, Maeder M L, Kaini P, Sander J D, Joung J K, Peterson R T, Yeh J R. Heritable and precise zebrafish genome editing using a CRISPR-cas system. PLoS One 2013; 8:e68708.
69. Irion U, Krauss J, Nusslein-Volhard C. Precise and efficient genome editing in zebrafish using the CRISPR/Cas9 system. Development 2014; 141:4827-30.
70. Armstrong G A, Liao M, You Z, Lissouba A, Chen B E, Drapeau P. Homology directed knockin of point mutations in the zebrafish tardbp and fus genes in ALS using the CRISPR/Cas9 system. PLoS One 2016; 11:e0150188.
71. Lessieur E M, Fogerty J, Gaivin R J, Song P, Perkins B D. The ciliopathy gene ahi1 is required for zebrafish cone photoreceptor outer segment morphogenesis and survival. Invest. Ophthalmol. Vis. Sci. 2017; 58:448-60.
72. Van De Weghe J C, Rusterholz T D S, Latour B, Grout M E, Aldinger K A, Shaheen R, Dempsey J C, Maddirevula S, Cheng Y H, Phelps I G, Gesemann M, Goel H, Birk O S, Alanzi T, Rawashdeh R, Khan A O, University of Washington Center for Mendelian Genomics, Bamshad M J, Nickerson D A, Neuhauss S C F, Dobyns W B, Alkuraya F S, Roepman R, Bachmann-Gagescu R, Doherty D. Mutations in ARMC9, which encodes a basal body protein, cause joubert syndrome in humans and ciliopathy phenotypes in zebrafish. Am. J. Hum. Genet. 2017; 101:23-36.
73. Morrow J M, Lazic S, Chang B S. A novel rhodopsin-like gene expressed in zebrafish retina. Vis. Neurosci. 2011; 28:325-35.
74. Morrow J M, Lazic S, Dixon Fox M, Kuo C, Schott R K, de A Gutierrez E, Santini F, Tropepe V, Chang B S. A second visual rhodopsin gene, rh1-2, is expressed in zebrafish photoreceptors and found in other ray-finned fishes. J. Exp. Biol. 2017; 220:294-303.
75. Hyatt G A, Schmitt E A, Fadool J M, Dowling J E. Retinoic acid alters photoreceptor development in vivo. Proc. Natl. Acad. Sci. U.S.A. 1996; 93:13298-303.
76. Fadool J M. Development of a rod photoreceptor mosaic revealed in transgenic zebrafish. Dev. Biol. 2003; 258:277-90.
77. Ile K E, Kassen S, Cao C, Vihtehlic T, Shah S D, Mousley C J, Alb J G, Jr, Huijbregts R P, Stearns G W, Brockerhoff S E, Hyde D R, Bankaitis V A. Zebrafish class 1 phosphatidylinositol transfer proteins: PITPbeta and double cone cell outer segment integrity in retina. Traffic 2010; 11:1151-67.
78. Johns P R. Growth of the adult goldfish eye. III. source of the new retinal cells. J. Comp. Neurol. 1977; 176:343-57.
79. Stenkamp D L. Neurogenesis in the fish retina. Int. Rev. Cytol. 2007; 259:173-224.
80. Hartong D T, Berson E L, Dryja T P. Retinitis pigmentosa. Lancet 2006; 368:1795-809.
81. Rosenfeld P J, Cowley G S, McGee T L, Sandberg M A, Berson E L, Dryja T P. A null mutation in the rhodopsin gene causes rod photoreceptor dysfunction and autosomal recessive retinitis pigmentosa. Nat. Genet. 1992; 1:209-13.
82. Humphries M M, Rancourt D, Farrar G J, Kenna P, Hazel M, Bush R A, Sieving P A, Sheils D M, McNally N, Creighton P, Erven A, Boros A, Gulya K, Capecchi M R, Humphries P. Retinopathy induced in mice by targeted disruption of the rhodopsin gene. Nat. Genet. 1997; 15:216-9.
83. Frederick J M, Krasnoperova N V, Hoffmann K, Church-Kopish J, Ruther K, Howes K, Lem J, Baehr W. Mutant rhodopsin transgene expression on a null background. Invest. Ophthalmol. Vis. Sci. 2001; 42:826-33.
84. Concepcion F, Chen J. Q344ter mutation causes mislocalization of rhodopsin molecules that are catalytically active: A mouse model of Q344ter-induced retinal degeneration. PLoS One 2010; 5:e10904.
85. Nelson S M, Frey R A, Wardwell S L, Stenkamp D L. The developmental sequence of gene expression within the rod photoreceptor lineage in embryonic zebrafish. Dev. Dyn. 2008; 237:2903-17.
86. Chen J, Rattner A, Nathans J. The rod photoreceptor-specific nuclear receptor Nr2e3 represses transcription of multiple cone-specific genes. J. Neurosci. 2005; 25:118-29.
87. Larison K D, Bremiller R. Early onset of phenotype and cell patterning in the embryonic zebrafish retina. Development 1990; 109:567-76.
88. Raymond P A, Barthel L K, Curran G A. Developmental patterning of rod and cone photoreceptors in embryonic zebrafish. J. Comp. Neurol. 1995; 359:537-50.
89. Hu M, Easter S S. Retinal neurogenesis: The formation of the initial central patch of postmitotic cells. Dev. Biol. 1999; 207:309-21.
90. Schmitt E A, Dowling J E. Comparison of topographical patterns of ganglion and photoreceptor cell differentiation in the retina of the zebrafish, *Danio rerio*. J. Comp. Neurol. 1996; 371:222-34.
91. Robinson J, Schmitt E A, Dowling J E. Temporal and spatial patterns of opsin gene expression in zebrafish (*Danio rerio*). Vis. Neurosci. 1995; 12:895-906.
92. Schmitt E A, Dowling J E. Early retinal development in the zebrafish, *Danio rerio*: Light and electron microscopic analyses. J. Comp. Neurol. 1999; 404:515-36.
93. Branchek T, Bremiller R. The development of photoreceptors in the zebrafish, brachydanio *rerio*. I. structure. J. Comp. Neurol. 1984; 224:107-15.
94. Branchek T. The development of photoreceptors in the zebrafish, brachydanio *rerio*. II. function. J. Comp. Neurol. 1984; 224:116-22.
95. Easter S S, Jr, Nicola G N. The development of vision in the zebrafish (*Danio rerio*). Dev. Biol. 1996; 180:646-63.
96. Akimoto M, Cheng H, Zhu D, Brzezinski J A, Khanna R, Filippova E, Oh E C, Jing Y, Linares J L, Brooks M, Zareparsi S, Mears A J, Hero A, Glaser T, Swaroop A. Targeting of GFP to newborn rods by nrl promoter and temporal expression profiling of flow-sorted photoreceptors. Proc. Natl. Acad. Sci. U.S.A. 2006; 103:3890-5.

97. Morrow E M, Belliveau M J, Cepko C L. Two phases of rod photoreceptor differentiation during rat retinal development. J. Neurosci. 1998; 18:3738-48.

99. Adekeye, A., Haeri, M., Solessio, E., and Knox, B. E. (2014). Ablation of the proapoptotic genes chop or Ask1 does not prevent or delay loss of visual function in a P23H transgenic mouse model of retinitis pigmentosa. PLoS One 2, e83871.

100. Bedell, V. M., Wang, Y., Campbell, J. M., Poshusta, T. L., Starker, C. G., Krug, R. G., 2nd, Tan, W., Penheiter, S. G., Ma, A. C., Leung, A. Y. et al. (2012). In vivo genome editing using a high-efficiency TALEN system. Nature 7422, 114-118.

101. Berson, E. L., Rosner, B., Weigel-DiFranco, C., Dryja, T. P., and Sandberg, M. A. (2002). Disease progression in patients with dominant retinitis pigmentosa and rhodopsin mutations. Invest. Ophthalmol. Vis. Sci. 9, 3027-3036.

102. Cade, L., Reyon, D., Hwang, W. Y., Tsai, S. Q., Patel, S., Khayter, C., Joung, J. K., Sander, J. D., Peterson, R. T., and Yeh, J. R. (2012). Highly efficient generation of heritable zebrafish gene mutations using homo- and heterodimeric TALENs. Nucleic Acids Res. 16, 8001-8010.

103. Chen, S., Oikonomou, G., Chiu, C. N., Niles, B. J., Liu, J., Lee, D. A., Antoshechkin, I., and Prober, D. A. (2013). A large-scale in vivo analysis reveals that TALENs are significantly more mutagenic than ZFNs generated using context-dependent assembly. Nucleic Acids Res. 4, 2769-2778.

104. Choudhury, S., Nashine, S., Bhootada, Y., Kunte, M. M., Gorbatyuk, O., Lewin, A. S., and Gorbatyuk, M. (2014). Modulation of the Rate of Retinal Degeneration in T17M RHO Mice by Reprogramming the Unfolded Protein Response. Adv. Exp. Med. Biol. 455-462.

105. Ciruna B, Weidinger G, Knaut H, Thisse B, Thisse C, Raz E, Schier A F. (2002) Production of maternal-zygotic mutant zebrafish by germ-line replacement. Proc Natl Acad Sci USA. 99, 14919-24.

106. Gorbatyuk, M. S., Knox, T., LaVail, M. M., Gorbatyuk, O. S., Noorwez, S. M., Hauswirth, W. W., Lin, J. H., Muzyczka, N., and Lewin, A. S. (2010). Restoration of visual function in P23H rhodopsin transgenic rats by gene delivery of BiP/Grp78. Proc. Natl. Acad. Sci. U.S.A. 13, 5961-5966.

107. Huang, P., Xiao, A., Zhou, M., Zhu, Z., Lin, S., and Zhang, B. (2011). Heritable gene targeting in zebrafish using customized TALENs. Nat. Biotechnol. 8, 699-700.

108. Marc, R. E., Jones, B. W., Watt, C. B., and Strettoi, E. (2003). Neural remodeling in retinal degeneration. Prog. Retin. Eye Res. 5, 607-655.

109. Montana, C. L., Kolesnikov, A. V., Shen, S. Q., Myers, C. A., Kefalov, V. J., and Corbo, J. C. (2013). Reprogramming of adult rod photoreceptors prevents retinal degeneration. Proc. Natl. Acad. Sci. U.S.A. 5, 1732-1737.

110. Moritz, O. L., and Tam, B. M. (2010). Recent insights into the mechanisms underlying light-dependent retinal degeneration from X. laevis models of retinitis pigmentosa. Adv. Exp. Med. Biol. 509-515.

111. Peal, D. S., Peterson, R. T., and Milan, D. (2010). Small molecule screening in zebrafish. J. Cardiovasc. Transl. Res. 5, 454-460.

112. Perkins, B. D., Fadool, J. M., and Dowling, J. E. (2004). Photoreceptor structure and development: analyses using GFP transgenes. Methods Cell Biol. 315-331.

113. Peterson, R. T., Link, B. A., Dowling, J. E., and Schreiber, S. L. (2000). Small molecule developmental screens reveal the logic and timing of vertebrate development. Proc. Natl. Acad. Sci. U.S.A. 24, 12965-12969.

114. Peterson, R. T., Shaw, S. Y., Peterson, T. A., Milan, D. J., Zhong, T. P., Schreiber, S. L., MacRae, C. A., and Fishman, M. C. (2004). Chemical suppression of a genetic mutation in a zebrafish model of aortic coarctation. Nat. Biotechnol. 5, 595-599.

115. Rivolta, C., Sharon, D., DeAngelis, M. M., and Dryja, T. P. (2002). Retinitis pigmentosa and allied diseases: numerous diseases, genes, and inheritance patterns. Hum. Mol. Genet. 10, 1219-1227.

116. Roger, J. E., Ranganath, K., Zhao, L., Cojocaru, R. I., Brooks, M., Gotoh, N., Veleri, S., Hiriyanna, A., Rachel, R. A., Campos, M. M. et al. (2012). Preservation of cone photoreceptors after a rapid yet transient degeneration and remodeling in cone-only Nrl−/− mouse retina. J. Neurosci. 2, 528-541.

117. Ross, J. W., Fernandez de Castro, J. P., Zhao, J., Samuel, M., Walters, E., Rios, C., Bray-Ward, P., Jones, B. W., Marc, R. E., Wang, W. et al. (2012). Generation of an inbred miniature pig model of retinitis pigmentosa. Invest. Ophthalmol. Vis. Sci. 1, 501-507.

1184. Sander, J. D., Cade, L., Khayter, C., Reyon, D., Peterson, R. T., Joung, J. K., and Yeh, J. R. (2011). Targeted gene disruption in somatic zebrafish cells using engineered TALENs. Nat. Biotechnol. 8, 697-698.

119. Tamplin, O. J., White, R. M., Jing, L., Kaufman, C. K., Lacadie, S. A., Li, P., Taylor, A. M., and Zon, L. I. (2012). Small molecule screening in zebrafish: swimming in potential drug therapies. Wiley Interdiscip. Rev. Dev. Biol. 3, 459-468.

120. Wright, A. F., Chakarova, C. F., Abd El-Aziz, M. M., and Bhattacharya, S. S. (2010). Photoreceptor degeneration: genetic and mechanistic dissection of a complex trait. Nat. Rev. Genet. 4, 273-284.

121. Yoshimatsu, T., Williams, P. R., D'Orazi, F. D., Suzuki, S. C., Fadool, J. M., Allison, W. T., Raymond, P. A., and Wong, R. O. (2014). Transmission from the dominant input shapes the stereotypic ratio of photoreceptor inputs onto horizontal cells. Nat. Commun. 3699.Bedel.

What is claimed is:

1. A non-naturally occurring zebrafish comprising one or more mutations in rhodopsin (rho) locus, wherein said one or more mutations leads to rod degeneration, and further wherein said zebrafish comprises an exogenous nucleic acid encoding a reporter protein that is operably linked to a *Xenopus* opsin (Xops) promoter; wherein the zebrafish exhibits photoreceptor degeneration phenotype analogous to humans.

2. The zebrafish of claim 1, wherein the mutation or mutations disrupts sites essential for protein-protein interaction or trafficking.

3. The zebrafish of claim 1, wherein the mutation or mutations leads to altered protein folding.

4. The zebrafish of claim 1, wherein the mutation or mutations disrupts a consensus sequence for protein glycosylation.

5. The zebrafish of claim 1, wherein the mutation comprises SEQ ID NO: 2, 3, 8, 9, 10, or 11.

6. The zebrafish of claim 1, wherein the reporter protein is a fluorescent protein.

7. The zebrafish of claim 1, wherein the zebrafish further comprises a mutation in the pde6c gene.

8. The zebrafish of claim 7, wherein the zebrafish are homozygous for the mutant pde6c allele.

9. The zebrafish of claim 1, wherein the zebrafish are embryos' larvae, juveniles and adults.

* * * * *